United States Patent
Reginald et al.

(10) Patent No.: US 10,316,291 B2
(45) Date of Patent: Jun. 11, 2019

(54) IMMUNO-ONCOLOGY MESODERMAL PROGENITOR (IOMP) CELL

(71) Applicant: Cell Therapy Limited, Cardiff (GB)

(72) Inventors: Ajan Reginald, Cardiff (GB); Sabena Sultan, Cardiff (GB); Martin John Evans, Cardiff (GB)

(73) Assignee: Cell Therapy Limited, Cardiff (GB)

( * ) Notice: Subject to any disclaimer, the term of this patent is extended or adjusted under 35 U.S.C. 154(b) by 0 days.

(21) Appl. No.: 15/748,571

(22) PCT Filed: Aug. 5, 2016

(86) PCT No.: PCT/GB2016/052447
§ 371 (c)(1),
(2) Date: Jan. 29, 2018

(87) PCT Pub. No.: WO2017/025729
PCT Pub. Date: Feb. 16, 2017

(65) Prior Publication Data
US 2018/0216073 A1 Aug. 2, 2018

(30) Foreign Application Priority Data

Aug. 7, 2015 (GB) .................................. 1513996.7

(51) Int. Cl.
*C12N 5/0775* (2010.01)
(52) U.S. Cl.
CPC ........ *C12N 5/0663* (2013.01); *C12N 2500/02* (2013.01); *C12N 2500/05* (2013.01); *C12N 2500/32* (2013.01); *C12N 2500/40* (2013.01); *C12N 2500/84* (2013.01); *C12N 2500/90* (2013.01)
(58) Field of Classification Search
CPC ............ C12N 2506/02; C12N 2506/03; C12N 5/0018; C12N 5/0607; C12N 5/0623; C12N 5/0647; C12N 5/0662; C12N 15/1058; C12N 2500/90; C12N 2501/10; C12N 2506/1346; C12N 5/0657; C12N 5/0665; C12N 5/0669; C12N 5/0672; C12N 5/0691; C12N 5/0692; C12N 5/0633; C12N 5/0634; C12N 2506/1353; C12N 5/078; A61K 35/28
See application file for complete search history.

(56) References Cited

U.S. PATENT DOCUMENTS 5,198,357 A    3/1993   Holmqvist et al.

FOREIGN PATENT DOCUMENTS

| WO | 2008156728 A1 | 12/2008 |
| WO | 2012111997 A2 | 8/2012 |
| WO | 2013005053 A2 | 1/2013 |
| WO | 2013076507 A2 | 5/2013 |
| WO | 2013149211 A2 | 10/2013 |
| WO | 2015189586 A1 | 12/2015 |
| WO | 2015189587 A1 | 12/2015 |

OTHER PUBLICATIONS

Anastasiadis K, Antonitsis P, Westaby S, Reginald A, Sultan S, Doumas A, et. al. Implantation of a Novel Allogeneic Mesenchymal Precursor Cell Type in Patients with Ischemic Cardiomyopathy Undergoing Coronary Artery Bypass Grafting: an Open Label Phase IIa Trial. J Cardiovasc Transl Res. Jun. 2016; 9(3):202-13.*
Akbarzadeh et al., "Liposome: classification, preparation, and applications", Nanoscale Research Letters. 8:102, (2013).
Capelli et al., "Human platelet lysate allows expansion and clinical grade production of mesenchymal stromal cells from small samples of bone marrow aspirates or marrow filter washouts", Bone Marrow Transplantation, Oct. 1, 2007, vol. 40, No. 8, pp. 785-791.
Carrancio et al. "Optimization of mesenchymal stem cell expansion procedures by cell separation and culture conditions modification", Experimental Hematology, Aug. 1, 2008, vol. 36, No. 8, pp. 1014-1021.
Elmore, "Apoptosis: A Review of Programmed Cell Death", (2007) Toxicol Pathology. 35(4): 495-516.
"ESGCT and FSGT Collaborative Congress Helsinki, Finland Sep. 17-20, 2015 Abstracts", Human Gene Therapy, Sep. 17, 2015.
Humphries et al., "Cell Adhesion Assays", Methods Mol Biol. (2009) 522: 203-210.
Meghana et al., "Liposomes: As a Topical Drug Delivery System", International Journal of Pharmaceutical and Chemical Sciences. (2012) 1(1): 1-10.
Muller and Luscinskas "Assays of Transendothelial Migration in vitro", Methods Enzymol. (2008) 443: 155-176.
Sirsi and Borden, "Microbubble Compositions, Properties and Biomedical Applications", Bubble Sci Eng Technol. (2009) 1(1-2): 3-17.
Sugie et al., "Zoledronic Acid-Induced Expansion of ?? T Cells from Early-Stage Breast Cancer Patients: Effect of IL-18 on Helper NK Cells", Cancer Immunol. Immunother. (2013) 62(4): 677-687.
Sultan et al., "Isolation of immunomodulatory progenitor cells (iMPs) of mesodermal lineage", Human Gene Therapy. 26 (2015).
Zaim et al., "Donor age and long-term culture affect differentiation and proliferation of human bone marrow mesenchymal stem cells", Ann Hematol. (2012) 91(8): 1175-1186.
Zaritskaya, "New flow cytometric assays for monitoring cell-mediated cytotoxicity", Expert Rev Vaccines. (2010) 9(6): 601-616.
Wu et al., "yo T Cells and Their Potential for Immunotherapy", (2014) Int J Biol Sci. 10(2): 119-135.
Holzwarth et al., "Low physiologic oxygen tensions reduce proliferation and differentiation of human multipotent mesenchymal stromal cells", BMC Cell Biology. (2010) Article 11.

* cited by examiner

*Primary Examiner* — Rachel B Gill
(74) *Attorney, Agent, or Firm* — Norton Rose Fulbright US LLP

(57) ABSTRACT

The invention relates to immuno-oncology mesodermal progenitor (ioMP) cells and their use in therapy.

3 Claims, No Drawings

IMMUNO-ONCOLOGY MESODERMAL PROGENITOR (IOMP) CELL

CROSS REFERENCE TO RELATED APPLICATIONS

This application is a national phase application under 35 U.S.C. § 371 that claims priority to International Application No. PCT/GB2016/052447 filed Aug. 5, 2016, which claims priority to Great Britain Patent Application No. 1513996.7 filed Aug. 7, 2015, all of which are incorporated herein by reference in their entirety.

FIELD OF THE INVENTION

The invention relates to immuno-oncology mesodermal progenitor (ioMP) cells and their use in therapy.

BACKGROUND TO THE INVENTION

Mesodermal cells are derived from a number of tissues and act as the supportive structure for other cell types. Bone marrow for instance is made of both haematopoietic and mesenchymal derived cells. Two principle mesenchymal cell types have been previously described and characterized, namely (i) mesenchymal stem cells (MSCs) and their precursors and (ii) mesenchymal precursor cells (MPCs) found in the bone marrow. Mesenchymal stem cells (MSCs) are multipotent, adult stem cells. MSCs differentiate to form the different specialised cells found in the skeletal tissues. For example, they can differentiate into cartilage cells (chondrocytes), bone cells (osteoblasts) and fat cells (adipocytes).

MSCs are already used in a variety of therapies, such as the treatment of Age-related Macular Degeneration (AMD) and myocardial infarct. Once administered to the subject, the MSCs typically migrate (or home) to the damaged tissue and exert their therapeutic effects through paracrine signaling and by promoting survival, repair and regeneration of the neighbouring cells in the damaged tissue.

There is some evidence to suggest that MSCs may possess certain immunosuppressive and immune-enhancing properties. MSCs could therefore be used to manipulate immune responses and thereby treat diseases. However, current therapies typically involve the infusion of a mixture of MSC subtypes, most of which do not possess the required immuno-modulatory properties. This necessitates the use of a high cell-dose which can lead to off-target side effects and volume-related side effects. Furthermore, MSCs are typically obtained from bone marrow and so it is difficult to obtain the large numbers of cells needed for this approach.

SUMMARY OF THE INVENTION

This invention relates to a novel cell type that has not been previously identified or isolated, the immuno-oncology mesodermal progenitor (ioMP) cell. This ioMP cell is quite distinct and different to both MSCs and MPCs in its composition, function and characteristics, which impart an enhanced immuno-modulatory capability.

The inventors have surprisingly identified a new immuno-oncology mesodermal progenitor (ioMP) cell having a specific marker expression pattern. In particular, the ioMP cell expresses CD66e, CD121b, CD122, CD164, CD172a, CD203c, CD264, CD270, CD328, CD358, T cell receptor (TCR) gamma delta, FMC7 and ITGB7. The ioMP cell expresses significantly greater amounts of these markers than a MSC. The ioMP cell does not express detectable levels of HLA-ABC, MIC A/B, Notch2, CD360, CLIP, and CD11b. The ioMP cells of the invention can be isolated from mononuclear cells (MCs), such as peripheral blood MCs. The ioMP cells are capable of increasing or decreasing T cell responses in vitro and in vivo. The ioMP cells can also be use to treat a disease. For instance, the ioMP cells can be used to treat a disease (such as cancer) by increasing cytotoxic, helper or gamma delta T cell responses and/or decreasing regulatory T cell responses. Alternatively, the ioMP cells can be used to treat a disease (such an allergic, autoimmune or immune-mediated disease) by decreasing cytotoxic, helper or gamma delta T cell responses and/or increasing regulatory T cell responses. The ioMP cells are capable of homing, adherence, transmigration, proliferation, secreting pro-inflammatory and anti-inflammatory cytokines and pro-apoptotic and anti-apoptotic molecules, and cell-to-cell contact-dependent lysis. Furthermore, the ioMP cells can be used to improve the stability, viability or function of chimeric antigen receptor (CAR) expressing T cells.

Accordingly, the invention provides immuno-oncology mesodermal progenitor (ioMP) cell, wherein the cell expresses detectable levels of CD66e, CD121b, CD122, CD164, CD172a, CD203c, CD264, CD270, CD328, CD358, T cell receptor (TCR) gamma delta, FMC7 and ITGB7, and wherein the does not express detectable levels of HLA-ABC, MIC A/B, Notch2, CD360, CLIP, and CD11b.

The invention also provides:
a population of two or more ioMP cells of the invention;
a population of ioMP cells, wherein
(i) at least 60% of the cells in the population express detectable levels of CD66e,
(ii) at least 45% of the cells in the population express detectable levels of CD121b,
(iii) at least 35% of the cells in the population express detectable levels of CD122,
(iv) at least 50% of the cells in the population express detectable levels of CD164,
(v) at least 45% of the cells in the population express detectable levels of CD172a,
(vi) at least 35% of the cells in the population express detectable levels of CD203c,
(vii) at least 45% of the cells in the population express detectable levels of CD264,
(viii) at least 35% of the cells in the population express detectable levels of CD270,
(ix) at least 35% of the cells in the population express detectable levels of CD328,
(x) at least 50% of the cells in the population express detectable levels of CD358,
(ix) at least 45% of the cells in the population express detectable levels of TCR gamma delta,
(x) at least 95% of the cells in the population express detectable levels of FMC, and
(xi) at least 95% of the cells in the population express detectable level of ITGB7;
and wherein
(a) 0.5% or fewer of the cells in the population express detectable levels of HLA-ABC,
(b) 0.5% or fewer of the cells in the population express detectable levels of MIC A/B,
(c) 0.5% or fewer of the cells in the population express detectable levels of Notch2,
(d) 0.5% or fewer of the cells in the population express detectable levels of CD360,
(e) 0.5% or fewer of the cells in the population express detectable levels of CLIP, and (f) 0.1% or fewer of the cells in the population express detectable levels of CD11b;

a pharmaceutical composition comprising (a) an ioMP cell of the invention or a population of the invention and (b) a pharmaceutically acceptable carrier or diluent, one or more liposomes and/or one or more microbubbles;

a pharmaceutical composition comprising (a) an ioMP cell of the invention or a population of the invention; (b) an immune cell; (c) an antigen; and (d) a pharmaceutically acceptable carrier or diluent.

a method of producing a population of ioMP cells of the invention, comprising (a) culturing mononuclear cells (MCs) under conditions which induce the MCs to differentiate into ioMP cells and (b) harvesting and culturing those ioMP cells which have an expression pattern as defined above and thereby producing a population of the invention;

an in vitro method of increasing the activity of cytotoxic, helper or gamma delta T cells in response to an antigen, comprising incubating the T cells with the antigen and a population of the invention under conditions which increase the activity of the T cells;

primed cytotoxic, helper or gamma delta T cells produced using the above method;

an in vitro method of increasing the activity of regulatory T cells in response to an antigen, comprising incubating the T cells with the antigen and a population of the invention under conditions which increase the activity of the T cells;

primed regulatory T cells produced using the above method;

an in vitro method of decreasing the activity of cytotoxic, helper or gamma delta T cells in response to an antigen, comprising incubating the T cells with the antigen and a population of the invention under conditions which decrease the activity of the T cells;

suppressed cytotoxic, helper or gamma delta T cells produced using the above method;

an in vitro method of decreasing the activity of regulatory T cells in response to an antigen, comprising incubating the T cells with the antigen and a population of the invention under conditions which decrease the activity of the T cells;

suppressed regulatory T cells produced using the above method;

an in vivo method of increasing the activity of cytotoxic, helper or gamma delta T cells in response to an antigen, comprising administering a population or pharmaceutical composition of the invention to a subject under conditions which increase the activity of the T cells;

primed cytotoxic, helper or gamma delta T cells produced using the above method;

an in vivo method of increasing the activity of regulatory T cells in response to an antigen, comprising administering a population or pharmaceutical composition of the invention to a subject under conditions which increase the activity of the T cells;

primed regulatory T cells produced using the above method;

an in vivo method of decreasing the activity of cytotoxic, helper or gamma delta T cells in response to an antigen, comprising administering a population or pharmaceutical composition of the invention to a subject under conditions which decrease the activity of the T cells;

suppressed cytotoxic, helper or gamma delta T cells produced using the above method;

an in vivo method of decreasing the activity of regulatory T cells in response to an antigen, comprising administering a population or a pharmaceutical composition of the invention to a subject under conditions which decrease the activity of the T cells;

suppressed regulatory T cells produced using the above method according;

a method of treating a disease by increasing cytotoxic, helper or gamma delta T cell responses to an antigen in a subject, the method comprising administering to the subject:
(a) the population or pharmaceutical composition of the invention;
(b) the population or pharmaceutical composition of the invention and the primed cytotoxic, helper or gamma delta T cells of the invention; or
(c) the primed cytotoxic, helper or gamma delta T cells of the invention;

a method of treating a disease by decreasing regulatory T cell responses to an antigen in a subject, the method comprising administering to the subject:
(a) the population or pharmaceutical composition of the invention;
(b) the population or pharmaceutical composition of the invention and the suppressed regulatory T cells of the invention; or
(c) the suppressed regulatory T cells of the invention;

a method of treating a disease by decreasing regulatory T cell responses to an antigen in a subject, the method comprising administering to the subject:
(a) the population or pharmaceutical composition of the invention and the primed cytotoxic, helper or gamma delta T cells of the invention; or
(b) the primed cytotoxic, helper or gamma delta T cells of the invention;

a method of treating a disease by decreasing cytotoxic, helper or gamma delta T cell responses to an antigen in a subject, the method comprising administering to the subject:
(a) the population or pharmaceutical composition of the invention;
(b) the population or pharmaceutical composition of the invention and the suppressed cytotoxic, helper or gamma delta T cells of the invention; or
(c) the suppressed cytotoxic, helper or gamma delta T cells of the invention;

a method of treating a disease by increasing regulatory T cell responses to an antigen in a subject, the method comprising administering to the subject:
(a) the population or pharmaceutical composition of the invention;
(b) the population or pharmaceutical composition of the invention and the primed regulatory T cells of the invention; or
(c) the primed regulatory T cells of the invention;

a method of treating a disease by decreasing cytotoxic, helper or gamma delta T cell responses to an antigen in a subject, the method comprising administering to the subject:
(a) the population or pharmaceutical composition of the invention; and the primed regulatory T cells of the invention; or
(b) the primed regulatory T cells of the invention;

a method of treating cancer in a subject, the method comprising administering to the subject the population or pharmaceutical composition of the invention;

a method of treating an allergic, autoimmune or immune-mediated disease in a subject, the method comprising administering to the subject the population or pharmaceutical composition of the invention; and a method of improving the potency, viability or stability of CAR T cells, comprising incubating CAR T cells in the presence of a population of the invention.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "a tissue" includes two or more such tissues, reference to "a subject" includes two or more such subjects, and the like.

All publications, patents and patent applications cited herein, whether supra or infra, are hereby incorporated by reference in their entirety.

ioMP Cell of the Invention

The present invention provides an immuno-oncology mesodermal progenitor (ioMP) cell. The ioMP cell expresses detectable levels of CD66e, CD121b, CD122, CD164, CD172a, CD203c, CD264, CD270, CD328, CD358, T cell receptor (TCR) gamma delta, FMC7 and ITGB7. The ioMP cell does not express detectable levels of HLA-ABC, MIC A/B, Notch2, CD360, CLIP, and CD11b.

CD66e (alternative name Carcinoembryonic Antigen-related Cell Adhesion Molecule 5, CEACAM-5) functions as a calcium independent adhesion molecule through homophilic and heterophilic interactions with CEACAM-1. CD66e promotes cell migration, invasion and adhesion, and blocks apoptosis following loss of extra-cellular matrix (ECM) anchorage (anoikis).

CD121b (alternative name Interleukin 1 receptor type II, IL1R2) binds interleukin alpha (IL1A), interleukin beta (IL1B) and interleukin 1 receptor type I (IL1R1/IL1RA) and acts as a decoy receptor that inhibits the activity of its ligands. Interleukin 4 (IL-4) is reported to antagonize the activity of interleukin 1 by inducing the expression and release of this cytokine.

Interleukin 2 (IL-2) binds to the IL-2 receptor, which has three forms. These three forms are generated by different combinations of three different proteins, often referred to as "chains": α (alpha) (also called IL-2Rα, CD25, or Tac antigen), β (beta) (also called IL-2Rβ, or CD122), and γ (gamma) (also called IL-2Rγ, γc, common gamma chain, or CD132). IL-2 and its receptor have important roles in key functions of the immune system, such as tolerance and immunity. The effects of IL-2 and its receptor are primarily mediated via their direct effects on T cells.

CD164 is also known as sialomucin core protein 24, and functions as a cell adhesion molecule. Sialomucins are a heterogeneous group of secreted or membrane-associated mucins that appear to play two key but opposing roles in vivo, firstly as cytoprotective or antiadhesive agents and secondly as adhesion receptors. CD164 may serve as a signalling receptor that regulates proliferation, adhesion and migration in progenitor cells. CD164 may also associate with the chemokine receptor CXCR4, possibly as a co-receptor for the CXCR4 ligand SDF-1alpha.

CD172a (alternative name signal regulatory protein α, SIRP α) is regulatory membrane glycoprotein from the SIRP family expressed mainly by myeloid cells and also by stem cells or neurons. SIRP α acts as inhibitory receptor and interacts with the broadly expressed transmembrane protein CD47 (also known as "don't eat me" signal). This interaction negatively controls effector function of innate immune cells such as host cell phagocytosis.

CD203c (otherwise known as ectonucleotide pyrophosphatase/phosphodiesterase family member 3) is one of a series of ectoenzymes that are involved in hydrolysis of extracellular nucleotides. These ectoenzymes possess ATPase and ATP pyrophosphatase activities and are type II transmembrane proteins.

CD264 is a membrane receptor for CD253 (TNF-related apoptosis-inducing ligand, TRAIL) and is thought to act as a decoy receptor by competing for binding with other TRAIL receptors and inhibiting TRAIL-induced apoptosis. CD264 does not induce apoptosis, and has been shown to play an inhibitory role in TRAIL-induced cell apoptosis.

CD270 is a type I transmembrane protein and a member of the TNFR-TNF superfamily. CD270 interaction on T cells provides a costimulatory signal via CD270 signalling. CD270 has been reported to be involved in the induction of cytokines and matrix metalloproteinases.

CD328 (alternative name sialic acid-binding Ig-like lectin 7, SIGLEC7) is a putative adhesion molecule that mediates sialic-acid dependent binding to cells. CD328 mediates the inhibition of the cytotoxic function of natural killer (NK) cells. CD328 also inhibits the differentiation of CD34+ cell precursors towards the myelomonocytic cell lineage, and the in vitro proliferation of leukemic myeloid cells in vitro.

CD358 (also known as death receptor 6, DR6, or TNFRSF21) is a member of the tumour necrosis factor receptor superfamily. CD358 activates nuclear factor kappa-B and mitogen-activated protein kinase 8 and induces cell apoptosis. Knockout studies in mice suggest that this gene plays a role in T-helper cell activation, and may be involved in inflammation and immune regulation TCR-gamma delta is a T cell receptor (TCR) comprising gamma and delta TCR chains. TCRs discriminate foreign from self-peptides presented by major histocompatibility complex (MHC) class II molecules and essential for effective adaptive immune responses. T cells expressing TCR-gamma delta are known as gamma-delta T cells. Gamma delta T cells have shown anti-tumour and immunoregulatory activity.

FMC7 is involved in the optimisation of the B-cell immune response, in particular against T-cell independent antigens.

ITGB7 mediates adhesive interactions of leukocytes.

The ioMP cells of the invention have numerous advantages. The key advantages will be summarized here. However, further advantages will become apparent from the discussion below.

The ioMP cells of the invention may advantageously be used to treat a disease in a subject. For example, the ioMP cells may be used to treat cancer in a subject. The ioMP cells may also be used to treat an allergic, autoimmune or immune-mediated disease in a subject.

The ioMP cells of the invention may treat disease via their direct effects. For example, the ioMP cells may kill cells via contact-dependent cell lysis. Preferably, the ioMP cells kill tumour cells via contact-dependent cell lysis. The ioMP cells may also secrete molecules that act on other cells. Such molecules may affect cell metabolism, proliferation, survival, function or signalling. For instance, the ioMP cells may secrete pro-inflammatory cytokines and/or anti-inflammatory cytokines. The ioMP cells may secrete pro-apoptotic molecules and/or anti-apoptotic molecules.

The ioMP cells of the invention may modulate immune responses. In other words, the ioMP cells may have immuno-modulatory effects. For example, the ioMPs may increase or decrease the activity of immune cells such as cytotoxic T cells, helper T cells, gamma delta T cells and regulatory T cells. Gamma delta T cells are preferred. The ioMP cells of the invention may therefore be used to treat disease in a subject by increasing or decreasing T cell responses. This is discussed in more detail below.

In addition, the ioMP cells of the invention may be used to modulate T cell activity in response to an antigen in vitro or in vivo. Accordingly, the ioMP cells may be used to produce a population of T cells having a modified activity in response to an antigen. For instance, the ioMP cells may be used to produce a population of primed or suppressed T cells. The primed or suppressed T cells may be used to treat a disease in a subject. Specifically, the primed or suppressed T cells may be used to treat disease in a subject by increasing or decreasing T cell activity. The primed or suppressed T cells may be administered to the subject alone or in combination with the ioMP cells.

The ioMP cells of the invention may also be used in a method of improving the potency, viability and/or the stability of chimeric antigen receptor (CAR) T cells. This is also discussed in more detail below.

As discussed in more detail below, the ioMP cells are produced from mononuclear cells (MCs), such as peripheral MCs, taken from an individual, such as a human individual. Since the ioMP cells are produced from MCs, they may be produced easily (such as from peripheral blood) and may be autologous for the subject to be treated, thereby avoiding the risk of immunological rejection by the subject.

It is possible, in principle, to produce an unlimited number of ioMP cells from a single individual, since various samples of MCs (i.e. various samples of blood) may be obtained. It is certainly possible to produce very large numbers of ioMP cells from a single individual. The ioMP cells of the invention can therefore be made in large numbers.

The ioMP cells of the invention are produced in clinically relevant conditions, for instance in the absence of trace amounts of endotoxins and other environmental contaminants, as well as animal products such as fetal calf serum. This makes the ioMP cells of the invention particularly suitable for administration to subjects.

Since the ioMP cells of the invention are produced from MCs, they are substantially homologous and may be autologous. They also avoid donor-to-donor variation, which frequently occurs with MSCs. Numerous populations of ioMP cells of the invention can be produced from a to single sample taken from the subject before any other therapy, such as chemotherapy or radiotherapy, has begun. Therefore, the ioMP cells of the invention can avoid any of the detrimental effects of those treatments.

The ioMP cells of the invention can be made quickly. ioMP cells can be produced from MCs in less than 30 days, such as in about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, about 9 days, about 8 days, about 7 days, about 6 days, about 5 days, about 4 days, about 3 days, about 2 days or about 1 day.

The production of ioMP cells from MCs avoids the moral and ethical implications involved with using mesenchymal stem cells MSCs derived from human embryonic stem cells (hESCs).

The ioMP cells of the invention are typically produced from human MCs. The ioMP cells of the invention are therefore typically human. Alternatively, the ioMP cells may be produced from MCs from other animals or mammals, for instance from commercially farmed animals, such as horses, cattle, sheep or pigs, from laboratory animals, such as mice or rats, or from pets, such as cats, dogs, rabbits or guinea pigs.

The ioMP cells of the invention can be identified as immuno-oncology mesodermal progenitor cells using standard methods known in the art, including expression of lineage restricted markers, structural and functional characteristics. The ioMP cells will express detectable levels of cell surface markers known to be characteristic of ioMP cells. These are discussed below.

The ioMP cells of the invention are capable of successfully completing differentiation assays in vitro to confirm that they are of mesodermal lineage. Such assays include, but are not limited to, adipogenic differentiation assays, osteogenic differentiation assays and neurogenic differentiation assays (Zaim M et al Ann Hematol. 2012 August; 91(8):1175-86).

The ioMP cells of the invention are not stem cells. In particular, they are not MSCs. They are terminally differentiated. Although they can be forced under the right conditions in vitro to differentiating, for instance into cartilage or bone cells, they typically do not differentiate in vivo. The ioMP cells of the invention preferably have their effects by (i) direct effects, such as contact-dependent cell lysis, secretion of cytokines and/or secretion of pro- or anti-apoptotic molecules; or (ii) modulation of immune responses or immune cell activity (i.e. immuno-modulatory effects). In contrast, stem cells typically treat disease by differentiating into replacement tissue.

The ioMP cells of the invention are typically characterised by a spindle-shaped morphology. The ioMP cells are typically fibroblast-like, i.e. they have a small cell body with a few cell processes that are long and thin. The cells are typically from about 10 to about 20 µm in diameter.

The ioMP cells of the invention are distinguished from known cells, including MSCs, via their marker expression pattern. The ioMPs express detectable levels of CD66e, CD121b, CD122, CD164, CD172a, CD203c, CD264, CD270, CD328, CD358, TCR gamma delta, FMC7 and ITGB7. The ioMPs preferably express an increased amount of these markers compared with MSCs. The ioMP cells preferably express an increased amount of all of the markers compared with MSCs. This can be determined by comparing the expression level/amount of the markers in an ioMP of the invention with the expression level/amount in an MSC using the same technique under the same conditions. Suitable MSCs are commercially available. The MSC used for comparison is preferably a human MSC. Human MSCs are commercially available from Mesoblast® Ltd, Osiris Therapeutics® Inc. or Lonza®. The human MSC is preferably obtained from Lonza®. Such cells were used for the comparison in the Example. The MSC may be derived from any of the animals or mammals discussed above.

The ioMP cells of the invention do not express detectable levels of HLA-ABC, MIC A/B, Notch2, CD360, CLIP and CD11b.

Standard methods known in the art may be used to determine the detectable expression or increased expression of various markers discussed above (and below). Suitable methods include, but are not limited to, immunocytochemistry, immunoassays, flow cytometry, such as fluorescence activated cells sorting (FACS), and polymerase chain reaction (PCR), such as reverse transcription PCR (RT-PCR). Suitable immunoassays include, but are not limited to, Western blotting, enzyme-linked immunoassays (ELISA), enzyme-linked immunosorbent spot assays (ELISPOT assays), enzyme multiplied immunoassay techniques, radioallergosorbent (RAST) tests, radioimmunoassays, radiobinding assays and immunofluorescence. Western blotting, ELISAs and RT-PCR are all quantitative and so can be used to measure the level of expression of the various markers if present. The use of high-throughput FACS (HT-FACS) is disclosed in the Example. The expression or increased expression of any of the markers disclosed herein is preferably done using HT-FACS. Antibodies and fluorescently-labelled antibodies for all of the various markers discussed herein are commercially-available.

The ioMP cells of the invention preferably demonstrate an antibody mean fluorescence intensity (MFI) of at least 410, such as at least 450 or at least 500 for CD66e; an MFI of at least 770, such as at least 800 or at least 850, for CD121b; an MFI of at least 365, such as at least 400 or at least 450, for CD122; an MFI of at least 455, such as at least 800 or at least 850, for CD164; an MFI of at least 363, such as at least 400 or at least 450, for CD172a; an MFI of at least 371 for CD203c; an MFI of at least 411, such as at least 450 or at least 500, for CD264; an MFI of at least 370, such as at least 400 or at least 450, for CD270; an MFI of at least 369, such as at least 400 or at least 450, for CD328; an MFI of at least 406, such as at least 450 or at least 500, for CD358; an MFI of at least 430, such as at least 450 or at least 500, for TCR gamma delta, an MFI of at least 3500, such as at least 3750 or at least 4000, for FMC7 and an MFI of at least 1500, such as at least 1750 or at least 2000 for ITGB7. Mean fluorescent intensity (MFI) is a measure of intensity, time average energy flux measured in watts per square meter. It is an SI unit. The MFI for each marker is typically measured using HT-FACS. The MFI for each marker is preferably measured using HT-FACS as described in the Example.

In addition to the markers specified above, the ioMP cells of the invention typically express detectable levels of one or more of the other markers shown in Table 1 in the Example, except for HLA-ABC, MIC A/B, Notch2, CD360, CLIP, and CD11b. The ioMP cells may express detectable levels of any number and combination of the markers in Table 1, except for HLA-ABC, MIC A/B, Notch2, CD360, CLIP, and CD11b. The ioMP cells preferably express detectable levels of all of the markers in Table 1, except for HLA-ABC, MIC A/B, Notch2, CD360, CLIP, and CD11b.

The ioMP cells preferably further express detectable levels of one or more of β2-microglobulin, CD10, CD13, CD29, CD47, CD44, CD49b, CD49c, CD49d, CD49e, CD51/CD61, CD55, CD58, CD59, CD61, CD63, CD73, CD81, CD82, CD90, CD91, CD92, CD95, CD98, CD105, CD108, CD111, CD115, CD119, CD120a, CD130, CD140b, CD147, CD148, CD151, CD155, CD166, CD175s, CD257, CD276, CD288, CD295, CD340, CD344, CD351, CD230, cadherin-11 (CDH11), and lymphotoxin beta receptor (LTBR. The ioMP cells may express detectable levels of any number and combination of these markers. The ioMP cells preferably express detectable levels of all of these markers.

The ioMP cells preferably express an increased amount of one or more of β2-microglobulin, CD10, CD13, CD29, CD47, CD44, CD49b, CD49c, CD49d, CD49e, CD51/CD61, CD55, CD58, CD59, CD61, CD63, CD73, CD81, CD82, CD90, CD91, CD92, CD95, CD98, CD105, CD108, CD111, CD115, CD119, CD120a, CD130, CD140b, CD147, CD148, CD151, CD155, CD166, CD175s, CD257, CD276, CD288, CD295, CD340, CD344, CD351, CD230, cadherin-11 (CDH11) and lymphotoxin beta receptor (LTBR compared with a MSC. The ioMP cells preferably express an increased amount of all of these markers compared with a MSC.

The ioMP cells preferably further express detectable levels of one or more of CD26, CD44, CD46, CD49a, CD54, CD110, CD137L, CD146, CD156b, CD178, CD186, CD193, CD196, CD201, CD202b, CD221, CD227, CD230, CD231, CD235a, CD245, CD252, CD256, CD267, CD272, CD283, CD286, CD290, CD300e, CD309, CD312, CD337, CD338, CD354, Podoplanin and SSEA-4. The ioMP cells may express detectable levels of any number and combination of these markers. The ioMP cells preferably express detectable levels of all of these markers.

The ioMP cells preferably express an increased amount of one or more of CD26, CD44, CD46, CD49a, CD54, CD110, CD137L, CD146, CD156b, CD178, CD186, CD193, CD196, CD201, CD202b, CD221, CD227, CD230, CD231, CD235a, CD245, CD252, CD256, CD267, CD272, CD283, CD286, CD290, CD300e, CD309, CD312, CD337, CD338, CD354, Podoplanin and SSEA-4 compared with a MSC. The ioMP cells preferably express an increased amount of all of these markers compared with a MSC.

The ioMP cells of the invention are preferably capable of having pro-inflammatory or anti-inflammatory effects in a diseased tissue of a subject. The ability of the ioMP cells of the invention to have pro-inflammatory or anti-inflammatory effects may be measured using standard assays known in the art. Suitable methods include, but are not limited to, enzyme-linked immunosorbent assays (ELISAs) for the secretion of cytokines, enhanced mixed leukocyte reactions and up-regulation of co-stimulatory molecules and maturation markers, measured by flow cytometry. Specific methods that may be used are disclosed in the Example. The cytokines measured are typically interleukins, such as interleukin-8 (IL-8), selectins, adhesion molecules, such as Intercellular Adhesion Molecule-1 (ICAM-1), and chemoattractant proteins, such as monocyte chemotactic protein-1 (MCP-1) and tumour necrosis factor alpha (TNF-alpha). Assays for these cytokines are commercially-available. Anti-inflammatory factors are preferably detected and measured using the Luminex® assay described in the Examples. Such assays are commercially available from Life Technologies®.

The ioMP cells preferably secrete detectable levels of one or more of interleukin-6 (IL-6), IL-8, C-X-C motif chemokine 10 (CXCL10; interferon gamma-induced protein 10; IP-10), Chemokine (C-C motif) ligand 2 (CCL2; monocyte chemotactic protein-1; MCP-1) and Chemokine (C-C motif) ligand 5 (CCL5; regulated on activation, normal T cell expressed and secreted; RANTES). The ioMP cells may secrete any number and combination of these factors. The ioMP cells preferably secrete all of these markers.

The ioMP cells preferably secrete an increased amount of one or more of IL-6, IL-8, IP-10, MCP-1 and RANTES compared with a MSC. The ioMP cells may secrete an increased amount of any number and combination of these factors. The ioMP cells preferably secrete an increased amount of all of these markers.

The ioMP cells preferably secrete a decreased amount of interleukin-10 (IL-10) and/or IL-12 compared with a mesenchymal stem cell MSC. IL-10 and IL-12 are pro-inflammatory cytokines.

Any of the ioMP cells of the invention may express detectable levels of one or more of (i) vascular endothelial growth factor (VEGF), (ii) transforming growth factor beta (TGF-beta), (iii) insulin-like growth factor-1 (IGF-1), (iv) fibroblast growth factor (FGF), (v) tumour necrosis factor alpha (TNF-alpha), (vi) interferon gamma (IFN-gamma) and (vii) interleukin-1 alpha (IL-1 alpha). Conditioned medium from cells overexpressing VEGF has been shown to alleviate heart failure in a hamster model. Hence, the IMP cells of the invention which express or express an increased amount of VEGF will have the same effect of diseased cardiac tissue.

The ioMP cells may express detectable levels of one or more of (i) to (vii). The ioMP cells of the invention may express an increased amount of one or more of (i) to (vii) compared with MSCs. Quantitative assays for cell markers are described above. The detectable expression of these markers and their level of expression may be measured as discussed above.

In the definition of (i) to (vii) given above, any combination of one or more of (i) to (vii) may be expressed or expressed in an increased amount. For instance, for each definition of (i) to (vii), the IMP cells may express detectable levels of, or express an increased amount of, (i); (ii); (iii); (iv); (v); (vi); (vii); (i) and (ii); (i) and (iii); (i) and (iv); (i) and (v); (i) and (vi); (i) and (vii); (ii) and (iii); (ii) and (iv); (ii) and (v); (ii) and (vi); (ii) and (vii); (iii) and (iv); (iii) and (v); (iii) and (vi); (iii) and (vii); (iv) and (v); (iv) and (vi); (iv) and (vii); (v) and (vi); (v) and (vii); (vi) and (vii); (i), (ii) and (iii); (i), (ii) and (iv); (i), (ii) and (v); (i), (ii) and (vi); (i), (ii) and (vii); (i,), (iii) and (iv); (i), (iii) and (v); (i), (iii) and (vi); (i), (iii) and (vii); (i), (iv) and (v); (i), (iv) and (vi); (i), (iv) and (vii); (i), (v) and (vi); (i), (v) and (vii); (i), (vi) and (vii); (ii), (iii) and (iv); (ii), (iii) and (v); (ii), (iii) and (vi); (ii), (iii) and (vii); (ii), (iv) and (v); (ii), (iv) and (vi); (ii), (iv) and (vii); (ii), (v) and (vi); (ii), (v) and (vii); (ii), (vi) and (vii); (iii), (iv) and (v); (iii), (iv) and (vi); (iii), (iv) and (vii); (iii), (v) and (vi); (iii), (v) and (vii); (iii), (vi) and (vii); (iv), (v) and (vi); (iv), (v) and (vii); (iv), (vi) and (vii); (v), (vi) and (vii); (i), (ii), (iii) and (iv); (i), (ii), (iii) and (v); (i), (ii), (iii) and (vi); (i), (ii), (iii) and (vii); (i), (ii), (iv) and (v); (i), (ii), (iv) and (vi); (i), (ii), (iv) and (vii); (i), (ii), (v) and (vi); (i), (ii), (v) and (vii); (i), (ii), (vi) and (vii); (i), (iii), (iv) and (v); (i), (iii), (iv) and (vi); (i), (iii), (iv) and (vii); (i), (iii), (v) and (vi); (i), (iii), (v) and (vii); (i), (iii), (vi) and (vii); (i), (iv), (v) and (vi); (i), (iv), (v) and (vii); (i), (iv), (vi) and (vii); (i), (v), (vi) and (vii); (ii), (iii), (iv) and (v); (ii), (iii), (iv) and (vi); (ii), (iii), (iv) and (vii); (ii), (iii), (v) and (vi); (ii), (iii), (v) and (vii); (ii), (iii), (vi) and (vii); (ii), (iv), (v) and (vi); (ii), (iv), (v) and (vii); (ii), (iv), (vi) and (vii); (ii), (v), (vi) and (vii); (iii), (iv), (v) and (vi); (iii), (iv), (v) and (vii); (iii), (iv), (vi) and (vii); (iii), (v), (vi) and (vii); (iv), (v), (vi) and (vii); (i), (ii), (iii), (iv) and (v); (i), (ii), (iii), (iv) and (vi); (i), (ii), (iii), (iv) and (vii); (i), (ii), (iii), (v) and (vi); (i), (ii), (iii), (v) and (vii); (i), (ii), (iii), (vi) and (vii); (i), (ii), (iv), (v) and (vi); (i), (ii), (iv), (v) and (vii); (i), (ii), (iv), (vi) and (vii); (i), (ii), (v), (vi) and (vii); (i), (iii), (iv), (v) and (vi); (i), (iii), (iv), (v) and (vii); (i), (iii), (iv), (vi) and vii); (i), (iii), (v), (vi) and (vii); (i), (iv), (v), (vi) and (vii); (ii), (iii), (iv), (v) and (vi); (ii), iii), (iv), (v) and (vii); (ii), (iii), (iv), (vi) and (vii); (ii), (iii), (v), (vi) and (vii); (ii), (iv), (v), (vi) and (vii); (iii), (iv), (v), (vi) and vii); (i), (ii), (iii), (iv), (v) and (vi); (i), (ii), (iii), (iv), (v) and (vii); (i), (ii), (iii), (iv), (vi) and (vii); (i), (ii), (iii), (v), (vi) and (vii); (i), (ii), (iv), (v), (vi) and (vii); (i), (iii), (iv), (v), (vi) and (vii); (ii), (iii), (iv), (v), (vi) and (vii); or (i), (ii), (iii), (iv), (v), (vi) and (vii). The combinations of (i) to (vii) are independently selectable from this list.

The ioMP cells of the invention preferably express and/or secrete detectable levels of interferon gamma (IFN-gamma). The ioMP cells of the invention preferably express and/or secrete an increased amount of IFN-gamma compared with a MSC. IFN-gamma expression or secretion may be determined using the methods set out above.

In addition to any of the markers discussed above, the ioMP cells of the invention preferably also express detectable levels of, LIF and/or platelet-derived growth factor (PDGF) receptors. The ioMP cells of the invention preferably express an increased amount of LIF and/or platelet-derived growth factor (PDGF) receptors compared with mesenchymal stem cells. The PDGF receptors are preferably PDGF-A receptors and/or PSDGF-B receptors. MSCs that have high expression of these receptors can migrate effectively into areas in which platelets have been activated, such as wounds and thrombotic vessels. The same will be true of ioMP cells expressing or expressing an increased amount of the receptors.

The ioMP cells of the invention are preferably capable of migrating to a specific tissue in a subject. In other words, when the cells are administered to a subject having a disease (such as cancer, an autoimmune or immune-mediated disease, or an allergic disease), the cells are capable of migrating or homing to the required tissue or tissues. The tissue may be a tissue that normally exists in a healthy subject. Alternatively, the tissue may be a tumour. This migratory capability of ioMP cells is advantageous because it means that the cells can be infused via standard routes, for instance intravenously, and will then target the site of disease. The cells do not have to be delivered to the diseased tissue.

The specific tissue is preferably cardiac, bone, cartilage, tendon, ligament, liver, kidney, brain, ovary, testicular, breast, lung or skin tissue. This applies not only to migration, but also adherence, transmigration, proliferation, anti-tumour effects, immune-modulatory effects, pro-inflammatory effects and anti-inflammatory effects as discussed in more detail above and below.

The ability of the ioMP cells of the invention to migrate to diseased tissue may be measured using standard assays known in the art. Suitable methods include, but are not limited to, genomic reverse transcription polymerase chain reaction (RT-PCR with or without reporter genes) and labelling techniques.

RT-PCR is the most straightforward and simple means to trace the ioMP cells of the invention within a subject. A transduced transgene or individual donor markers can be used for this purpose and transplanted cell-specific signals have been obtained in several subject studies. The results are generally semi-quantitative.

Alternatively, the ioMP cells of the invention may be stained with a dye of interest, such as a fluorescent dye, and may be monitored in the subject via the signal from the dye. Such methods are routine in the art.

Migration (or homing) is typically determined by measuring the number of cells that arrive at the damaged tissue. It may also be measured indirectly by observing the numbers of cells that have accumulated in the lungs (rather than the damaged tissue).

The ioMP cells of the invention are preferably capable of adhering to a specific, diseased tissue in a subject. Adherence and adhesion assay are known in the art (Humphries, Methods Mol Biol. 2009; 522:203-10).

The ioMP cells of the invention are preferably capable of transmigrating through the vascular endothelium to a specific, diseased tissue in a subject. Transmigration assays are known in the art (Muller and Luscinskas, Methods Enzymol. 2008; 443: 155-176).

The ioMP cells of the invention are preferably capable of exerting anti-tumour effects. As set out above, theses effects may be direct (e.g. by contact-dependent cell lysis, cytokine release, or regulation of apoptosis), or indirect (e.g. via immuno-modulation). Assays for cytokine secretion are described above. Assays for contact dependent cell lysis and apoptosis are well known in the art (Elmore, Toxcol Pathology, 2007; 35(4): 495-516; Zaritskaya, Expert Rev Vaccines. 2010 June; 9(6): 601-616).

The ioMP cells of the invention are preferably capable of immuno-modulation. Immuno-modulation is the modulation of an immune response or of the activity of an immune cell. Immuno-modulation may be achieved by a variety of mechanisms, For instance, the ioMP cells may secrete cytokines or inflammatory mediators that alter act on immune cells to alter their activity. The ioMP cells may also signal to immune cells by other means. For example, ligands on the ioMP cells may bind to receptors on target immune cells, triggering a signalling cascade. Methods for measuring cytokine secretion and marker (ligand) expression are discussed above. Methods of measuring immune cells signalling and activity are well known in the art. The ioMP cells preferably use the same pathways as T cells to regulate immune responses.

The ioMP cells of the invention are preferably autologous. In other words, the cells are preferably derived from the subject into which the cells will be administered. Alternatively, the ioMP cells are preferably allogeneic. In other words, the cells are preferably derived from a subject that is immunologically compatible with the subject into which the cells will be administered.

An ioMP cell of the invention may be isolated, substantially isolated, purified or substantially purified. The ioMP cell is isolated or purified if it is completely free of any other components, such as culture medium, other cells of the invention or other cell types. The ioMP cell is substantially isolated if it is mixed with carriers or diluents, such as culture medium, which will not interfere with its intended use. Alternatively, the ioMP cell of the invention may be present in a growth matrix or immobilized on a surface as discussed below.

ioMP cells of the invention may be isolated using a variety of techniques including antibody-based techniques. Cells may be isolated using negative and positive selection techniques based on the binding of monoclonal antibodies to those surface markers which are present on the ioMP cell (see above). Hence, the ioMP cells may be separated using any antibody-based technique, including fluorescent activated cell sorting (FACS) and magnetic bead separation.

As discussed in more detail below, the ioMP cells may be treated ex vivo. Thus the cells may be loaded or transfected with a therapeutic or diagnostic agent and then used therapeutically in the methods of the invention.

Population of the Invention

The invention also provides a population of two or more ioMP cells of the invention. Any number of cells may be present in the population. The population of the invention preferably comprises at least about $5 \times 10^5$ ioMP cells of the invention. The population more preferably comprises at least about $1 \times 10^6$, at least about $2 \times 10^6$, at least about 2.5 $2 \times 10^6$, at least about $5 \times 10^6$, at least about $1 \times 10^7$, at least about $2 \times 10^7$, at least about $5 \times 10^7$, at least about $1 \times 10^8$ or at least about $2 \times 10^8$ ioMP cells of the invention. In some instances, the population may comprise at least about $1.0 \times 10^7$, at least about $1.0 \times 10^8$, at least about $1.0 \times 10^9$, at least about $1.0 \times 10^{10}$, at least about $1.0 \times 10^{11}$ or at about least $1.0 \times 10^{12}$ ioMP cells of the invention or even more.

The population comprising two or more ioMP cells of the invention may comprise other cells in addition to the ioMP cells of the invention. However, at least 70% of the cells in the population are preferably ioMP cells of the invention. More preferably, at least about 75%, at least about 80%, at least about 85%, at least about 90%, at least about 97%, at least about 98% or at least about 99% of the cells in the population are ioMP cells of the invention.

The invention also provides specific populations of ioMP cells. The invention provides a population of ioMP cells, wherein (i) at least 60% of the cells in the population express detectable levels of CD66e, (ii) at least 45% of the cells in the population express detectable levels of CD121b, (iii) at least 35% of the cells in the population express detectable levels of CD122, (iv) at least 50% of the cells in the population express detectable levels of CD164, (v) at least 45% of the cells in the population express detectable levels of CD172a, (vi) at least 35% of the cells in the population express detectable levels of CD203c, (vii) at least 45% of the cells in the population express detectable levels of CD264, (viii) at least 35% of the cells in the population express detectable levels of CD270, (ix) at least 35% of the cells in the population express detectable levels of CD328, (x) at least 50% of the cells in the population express detectable levels of CD358, (xi) at least 45% of the cells in the population express detectable levels of TCR gamma delta, (xi) at least 95% of the cells in the population express detectable levels of FMC, and (xii) at least 95% of the cells in the population express detectable level of ITGB7;

and wherein (a) 0.5% or fewer of the cells in the population express detectable levels of HLA-ABC, (b) 0.5% or fewer of the cells in the population express detectable levels of MIC A/B, (c) 0.5% or fewer of the cells in the population express detectable levels of Notch2, (d) 0.5% or fewer of the cells in the population express detectable levels of CD360, (e) 0.5% or fewer of the cells in the population express detectable levels of CLIP, and (f) 0.1% or fewer of the cells in the population express detectable levels of CD11b.

The invention also provides a population of ioMP cells, wherein (i) at least 69% of the cells in the population express detectable levels of CD66e, (ii) at least 54% of the cells in the population express detectable levels of CD121b, (iii) at least 43% of the cells in the population express detectable levels of CD122, (iv) at least 60% of the cells in the population express detectable levels of CD164, (v) at least 56% of the cells in the population express detectable levels of CD172a, (vi) at least 47% of the cells in the population express detectable levels of CD203c, (vii) at least 55% of the cells in the population express detectable levels of CD264, (viii) at least 47% of the cells in the population express detectable levels of CD270, (ix) at least 43% of the cells in the population express detectable levels of CD328, (x) at least 62% of the cells in the population express detectable levels of CD358, (xi) at least 56% of the cells in the population express detectable levels of TCR gamma delta, (xi) at least 99% of the cells in the population express detectable levels of FMC, and (xii) at least 99% of the cells in the population express detectable level of ITGB7;

and wherein (a) 0.1% or fewer of the cells in the population express detectable levels of HLA-ABC, (b) 0.1% or fewer of the cells in the population express detectable levels of MIC A/B, (c) 0.2% or fewer of the cells in the population express detectable levels of Notch2, (d) 0.1% or fewer of the cells in the population express detectable levels of CD360, (e) 0.1% or fewer of the cells in the population express detectable levels of CLIP, and (f) 0.05% or fewer of the cells or none of the cells in the population express detectable levels of CD11b.

The cells in these preferred populations may further express detectable levels of any of the markers discussed above with reference to the ioMP of the invention. The cells in the these preferred populations may have any of the advantageous properties of the IMP cells discussed above.

At least 85%, such as at least 90% or at least 95%, of the cells in the population preferably express detectable levels of one or more of β2-microglobulin, CD10, CD13, CD29, CD47, CD44, CD49b, CD49c, CD49d, CD49e, CD51/CD61, CD55, CD58, CD59, CD61, CD63, CD73, CD81, CD82, CD90, CD91, CD92, CD95, CD98, CD105, CD108, CD111, CD115, CD119, CD120a, CD130, CD140b, CD147, CD148, CD151, CD155, CD166, CD175s, CD257, CD276, CD288, CD295, CD340, CD344, CD351, CD360, CD230, cadherin-11 (CDH11), and lymphotoxin beta receptor (LTBR). At least 85%, such as at least 90% or at least 95%, of the cells in the population may express detectable levels of any number and combination of these markers. At least 85%, such as at least 90% or at least 95%, of the cells in the population preferably express detectable levels of all of these markers.

At least 75%, such as at least 80% of the cells in the population preferably express detectable levels of one or more of CD49a, CD137L, CD146, CD178, CD202b, CD221, CD231, CD252, CD256, CD267, CD337 and SSEA-4. At least 75%, such as at least 80%, of the cells in the population may express detectable levels of any number and combination of these markers. At least 75%, such as at least 80%, of the cells in the population preferably express detectable levels of all of these markers.

At least 60%, such as at least 65% or at least 70%, of the cells in the population preferably express detectable levels of one or more of CD46f, CD54, CD110, CD186, CD193, CD201, CD245, CD272, CD283, CD286, CD290, CD300e, CD309, CD338, CD354 and Podoplanin. At least 60%, such as at least 65% or at least 70%, of the cells in the population may express detectable levels of any number and combination of these markers. At least 60%, such as at least 65% or at least 70%, of the cells in the population preferably express detectable levels of all of these markers.

At least 50%, such as at least 55% of the cells in the population preferably express detectable levels of one or more of CD26, CD196, CD227, CD235a and CD312. At least 50%, such as at least 55%, of the cells in the population may express detectable levels of any number and combination of these markers. At least 50%, such as at least 55%, of the cells in the population preferably express detectable levels of all of these markers.

At least 35%, such as at least 40%, of the cells in the population preferably express detectable levels of CD156b. CD156b is a type I transmembrane glycoprotein which belongs to the ADAM (a disintegrin and metalloprotease domain) family. CD156b is 125 kD, and functions as a tumour necrosis factor-alpha converting enzyme (TACE). CD156b also causes a number of inflammatory modulators to undergo ectodomain shedding, including TNFR75, IL-1RII, TNFR55, L-selectin, and the amyloid precursor protein among others. CD156b plays a prominent role in the activation of the Notch signalling pathway. CD156b is therefore a prospective therapeutic target in human cancer.

1% or fewer, such as 0.8% or fewer, 0.5%, 0.2% or fewer, or 0.1% or fewer, of the cells in the population preferably express detectable levels of one or more of CD1a, CD1b, CD1d, CD2, CD3e, CD4, CD5, CD7, CD8, CD11a, CD11c, CD14, CD15, CD18, CD184, CD19, CD20, CD21, CD22, CD23, CD24, CD27, CD28, CD3, CD30, CD31, CD32, CD33, CD34, CD35, CD352, CD357, CD36, CD37, CD38, CD39, CD40, CD41a, CD41b, CD42b, CD43, CD45, CD45RA, CD45RB, CD45RO, CD48, CD50, CD52, CD53, CD56, CD57, CD6, CD62E, CD62L, CD62P, CD64, CD65, CD66, CD66b, CD66d, CD69, CD70, CD72, CD74, CD75, CD77, CD79a, CD83, CD88, CD8b, CD94, CD97, CD100, CD101, CD102, CD103, CD104, CD109, CD117, CD127, CD129, CD131, CD133, CD136, CD137, CD138, CD142, CD144, CD154, CD158a, CD158b, CD158e2, CD159c, CD160, CD163, CD16b, CD171, CD172b, CD191, CD192, CD194, CD195, CD197, CD205, CD206, CD207, CD209, CD220, CD226, CD229, CD212, CD243, CD244, CD249, CD253, CD258, CD277, CD278, CD281, CD282, CD294, CD301, CD303, CD322, CD332, CD334, CD335, CD336, CD362, CDw199, CDw329, cadherin-6 (CDH6), DC immunoreceptor (DCIR), FMC7, HLA-A2, HLA-DM, HLA-DR, integrin beta-7 (ITGB7), leucine-rich repeat-containing G-protein coupled receptor 5 (Lgr-5), Notch1, Notch3, pro-caspase-activating compound 1 (PAC-1), Stro-1 and trophoblast glycoprotein (TPBG). 1% or fewer, such as 0.5% or fewer, of the cells in the population may express detectable levels of any number and combination of these markers. 1% or fewer, such as 0.5% or fewer, of the cells in the population preferably express detectable levels of all of these markers.

In any of the embodiments above where populations are defined with reference to % of cells expressing certain markers, the populations preferably comprise at least 5,000 cells, such as at least 6,000, at least 7,000, at least 8,000, at least 9,000, at least 10,000, at least 20,000, at least 30,000, at least 40,000 cells, at least 50,000 cells, at least 100,000 cells, at least 200,000 cells, at least 250,000 cells or at least 500,000 cells. The populations more preferably comprise at least 5000 cells, at least 50,000 cells or at least 250,000 cells. These populations may comprise any of the number of cells discussed above.

Any of the populations of cells disclosed herein may be diluted with other cells before use. For instance, the population may be combined with subject blood, mononuclear cells (MCs), MSCs, progenitor cells of the mesodermal lineage (PMLs), immuno-modulatory progenitor (IMP) cells, or a combination thereof. PMLs are disclosed in PCT/GB2012/051600 (published as WO 2013/005053). IMP cells are disclosed in PCT/GB2015/051673.

The populations of the invention are advantageous for therapy as discussed below. The ability to produce populations comprising large numbers of ioMP cells of the invention is one of the key advantages of the invention. The invention allows the treatment of subjects with a population of cells which can migrate efficiently to the tissue of interest and have anti-tumour, anti-inflammatory and/or immunomodulatory effects once there. This allows the use of a low cell-dose and avoids off-target side effects and volume-related side effects.

The population of the invention is preferably homologous. In other words, all of the IMP cells in the population are preferably genotypically and phenotypically identical. The population is preferably autologous or allogeneic as defined above.

However, the population can also be semi-allogeneic. Semi-allogeneic populations are typically produced from mononuclear cells from two or more subjects that are immunologically compatible with the subject into which the population will be administered. In other words, all of the cells in the population are preferably genetically identical or sufficiently genetically identical that the population is immunologically compatible with the subject into which the population will be administered. Since the ioMP cells of the invention may be derived from a subject, they may be autologous with the subject to be treated (i.e. genetically identical with the subject or sufficiently genetically identical that they are compatible for administration to the subject).

The population of the invention may be isolated, substantially isolated, purified or substantially purified. A population is isolated or purified if it is completely free of any other components, such as culture medium and other cells. A population is substantially isolated if it is mixed with carriers or diluents, such as culture medium, which will not interfere with its intended use. Other carriers and diluents are discussed in more detail below. A substantially isolated or substantially purified population does not comprise cells other than the ioMP cells of the invention. In some embodiments, the population of the invention may be present in a growth matrix or immobilized on a surface as discussed below.

The population is typically cultured in vitro. Techniques for culturing cells are well known to a person skilled in the art. The cells are may be cultured under standard conditions of 37° C., 5% $CO_2$ in medium without serum. The cells are preferably cultured under low oxygen conditions as discussed in more detail below. The cells may be cultured in any suitable flask or vessel, including wells of a flat plate such as a standard 6 well plate. Such plates are commercially available from Fisher scientific, VWR suppliers, Nunc, Starstedt or Falcon. The wells typically have a capacity of from about 1 ml to about 4 ml.

The flask, vessel or wells within which the population is contained or cultured may be modified to facilitate handling of the ioMP cells. For instance, the flask, vessel or wells may be modified to facilitate culture of the cells, for instance by including a growth matrix. The flask, vessel or wells may be modified to allow attachment of the ioMP cells or to allow immobilization of the ioMP cells onto a surface. One or more surfaces may be coated with extracellular matrix proteins such as laminin or collagen or any other capture molecules that bind to the cells and immobilize or capture them on the surface(s).

The population may be modified ex vivo using any of the techniques described herein. For instance, the population may be transfected or loaded with therapeutic or diagnostic agents. The population may then be used in the methods of treatment discussed in more detail below.

Method of Producing an ioMP Cell of the Invention

The invention also provides a method for producing a population of the invention. The method involves culturing mononuclear cells (MCs) under conditions which induce the MCs to differentiate into ioMP cells (step (a)). The method then involves harvesting and culturing the ioMP cells which expresses detectable levels of CD66e, CD121b, CD122, CD164, CD172a, CD203c, CD264, CD270, CD328, CD358, TCR gamma delta, FMC7 and ITGB7, and do not express detectable levels of HLA-ABC, MIC A/B, Notch2, CD360, CLIP, and CD11b. (step (b)). The harvested cells may express detectable levels of or increased amounts of any of the markers and factors described above with reference to the cells of the invention.

Mononuclear cells (MCs) and methods of isolating them are known in the art. The MCs may be primary MCs isolated from bone marrow. The MCs are preferably peripheral blood MCs (PBMCs), such as lymphocytes, monocytes and/or macrophages. PBMCs can be isolated from blood using a hydrophilic polysaccharide, such as Ficoll®. For instance, PBMCs may be isolated from blood using Ficoll-Paque® (a commercially-available density medium) as disclosed in the Example.

Before they are cultured, the MCs may be exposed to a mesenchymal stem cell enrichment cocktail. The cocktail preferably comprises antibodies that recognise CD3, CD14, CD19, CD38, CD66b (which are present on unwanted cells) and a component of red blood cells. Such a cocktail cross links unwanted cells with red blood cells forming immunorosettes which may be removed from the wanted MCs. A preferred cocktail is RosetteSep®.

Conditions suitable for inducing MCs to differentiate into mesenchymal cells (tissue mainly derived from the mesoderm) are known in the art. For instance, suitable conditions are disclosed in Capelli, C., et al. (Human platelet lysate allows expansion and clinical grade production of mesenchymal stromal cells from small samples of bone marrow aspirates or marrow filter washouts.

Bone Marrow Transplantation, 2007. 40: p. 785-791). These conditions may also be used to induce MCs to differentiate into ioMP cells in accordance with the invention. The MCs are may be cultured under standard conditions of 37° C., 5% $CO_2$ in medium without serum. MCs are typically seeded at a density of $1\times10^5$ cells $cm^2$.

The method preferably comprises culturing MCs with plasma lysate to induce the MCs to differentiate into ioMP cells. Platelet lysate refers to the combination of natural growth factors contained in platelets that has been released through lysing those platelets. Lysis can be accomplished through chemical means (i.e. $CaCl_2$), osmotic means (use of distilled $H_2O$) or through freezing/thawing procedures. Platelet lysate can be derived from whole blood as described in U.S. Pat. No. 5,198,357. Platelet lysate is preferably prepared as described in PCT/GB12/052911 (published as WO 2013/076507). The plasma lysate is preferably human plasma lysate.

In a preferred embodiment, step (a) of the method of the invention comprises culturing MCs in a medium comprising platelet lysate for sufficient time to induce the MCs to differentiate into ioMP cells. The sufficient time is typically from about 15 to about 25 days, preferably about 22 days. The medium preferably comprises about 20% or less platelet lysate by volume, such as about 15% or less by volume or about 10% or less by volume. The medium preferably comprises from about 5% to about 20% of platelet lysate by volume, such as from about 10% to about 15% by volume. The medium preferably comprises about 10% of platelet lysate by volume.

In another preferred embodiment, step (a) of the method of the invention comprises exposing MCs to a mesenchymal enrichment cocktail and then culturing the MCs in a medium comprising platelet lysate for sufficient time to induce the MCs to differentiate into ioMP cells. The sufficient time is typically from about 15 to about 25 days, preferably about 22 days.

In step (a), the medium is preferably Minimum Essential Medium (MEM). MEM is commercially available from various sources including Sigma-Aldrich. The medium preferably further comprises one or more of heparin, L-glutamine and penicillin/streptavidin (P/S). The L-glutamine may be replaced with GlutaMAX® (which is commercially-available from Life Technologies).

Step (a) preferably comprises culturing the MCs under conditions which allow the ioMP cells to adhere. Suitable conditions are discussed in more detail above.

In step (a), the MCs are preferably cultured under low oxygen conditions. The MCs are preferably cultured at less than about 20% oxygen (O2), such as less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2% or less than about 1% oxygen (O2). The MCs are preferably cultured at from about 0% to about 19% $O_2$, such as from about 1% to about 15% $O_2$, from about 2% to about 10% $O_2$ or from about 5% to about 8% $O_2$. The MCs are most preferably cultured at about 0% $O_2$. The figures for % oxygen (or % $O_2$) quoted above relate to % by volume of oxygen in the gas supplied to the cells during culture, for instance by the cell incubator. It is possible that some oxygen may leak into the incubator or enter when the door is opened.

In step (a), the MCs are most preferably cultured in the presence of platelet lysate and under low oxygen conditions. This combination mimics the natural conditions in the damaged tissue and so result in healthier and more therapeutically potent cells. Conventional cell culture is performed in 20% or 21% oxygen (approximately the atmospheric content) but there is no place in the human body that has this oxygen level. The epithelial cells in the lungs would "see" this oxygen level, but once the oxygen is dissolved and leaves the lungs, it decreases to around 17%. From there, it decreases even further to about 1-2% in the majority of the tissues, but being as low as 0.1% in avascular tissues such as the cartilage in the joints.

In step (a), the method preferably comprises culturing the MCs under conditions which induce the MCs to differentiate into immuno-modulatory progenitor (iMP) cells. This is described in International Patent Application No. PCT/GB2015/051673 (WO 2015/189587). The iMP cells express detectable levels of MIC A/B, CD304 (Neuropilin 1), CD178 (FAS ligand), CD289 (Toll-like receptor 9), CD363, (Sphingosine-1-phosphate receptor 1), CD99, CD181 (C-X-C chemokine receptor type 1; CXCR1), epidermal growth factor receptor (EGF-R), CXCR2 and CD126. The iMP cells also typically express detectable levels of CD29, CD44, CD73, CD90, CD105 and CD271 and do not express detectable levels of CD14, CD34 and CD45. Any of the culture conditions of step (a) discussed above can be used to differentiate MNCs into iMP cells, including any of, preferably all of, platelet lysate, adherence, and low oxygen.

In step (a), the method preferably further comprises culturing the iMP cells under conditions which epigenetically modify the iMP cells to form ioMP cells or induce the iMP cells to differentiate into ioMP cells. The conditions preferably comprise seeding the iMP cells at a density of about 6000 cell per cm$^2$ or lower, such as at a density of about 5500 cells per cm$^2$ or lower, about 5000 cells per cm$^2$ or lower or about 4500 cells per cm$^2$ or lower. The conditions preferably comprise increasing the CO2 above 5%, such as by at least about 0.1%, by at least about 0.2% or by at least about 0.3% (i.e. such as to at least about 5.1%, to at least about 5.2% or to at least about 5.3%). The conditions preferably comprise culturing the iMP cells at between about 5.1% and about 5.5% CO2, such as at about 5.2%, about 5.3% or about 5.4% CO2. The conditions preferably comprise culturing the iMP cells at about 5.3% CO2. The conditions preferably comprise decreasing the O2 by about 0.1% or lower, such as by about 0.05%. The conditions preferably comprise supplementing the medium with one or more of L-Alanine, Sodium Phosphate Monobasic (anhydrous) and 2'-Deoxyguanosine, such as L-Alanine; Sodium Phosphate Monobasic (anhydrous); 2'-Deoxyguanosine; L-Alanine and Sodium Phosphate Monobasic (anhydrous); L-Alanine and 2'-Deoxyguanosine; Sodium Phosphate Monobasic (anhydrous) and 2'-Deoxyguanosine; or L-Alanine, Sodium Phosphate Monobasic (anhydrous) and 2'-Deoxyguanosine.

In step (a), the method preferably further comprises culturing the iMP cells under conditions which epigenetically modify the iMP cells to form ioMP cells or which induce the iMP cells to differentiate into ioMP cells and which conditions comprise one or more of (i) seeding the iMP cells at a density of about 6000 cm$^2$ or lower, such as any of the densities discussed above, (ii) increasing the $CO_2$ above 5%, such as between about 5.1% and 5.5% or to about 5.1%, to about 5.2% or to about 5.3%, (iii) decreasing the O2 by about 0.1% or less, such as by about 0.05%, and (iv) supplementing the medium with one or more of L-Alanine, Sodium Phosphate Monobasic (anhydrous) and 2'-Deoxyguanosine, such as any of the combinations disclosed above. The conditions may comprise (i); (ii); (iii); (iv); (i) and (ii); (i) and (iii); (i) and (iv); (ii) and (iii); (ii) and (iv); (iii) and (iv); (i), (ii) and (iii); (i), (ii) and (iv); (i), (iii) and (iv); (ii), (iii) and (iv); or (i), (ii), (iii) and (iv).

In step (b), the method further comprises harvesting and culturing ioMP cells which have the necessary marker expression pattern as discussed above. The ioMP cells having the necessary marker expression pattern may be harvested using any antibody-based technique, including fluorescent activated cell sorting (FACS) and magnetic bead separation. FACS is preferred. HT-FACS is more preferred.

Any of the methods for culturing ioMP cells disclosed in relation to step (a) equally apply to step (b). In particular, the cells are cultured in step (b) in the presence of platelet lysate and under low oxygen conditions as discussed above in relation to step (a).

As will be clear from the discussion above, the method of the invention is carried out in clinically relevant conditions, i.e. in the absence of trace amounts of endotoxins and other environmental contaminants, such as lipopolysaccharides, lipopeptides and peptidoglycans, etc. This makes the ioMP cells of the invention particularly suitable for administration to subjects.

The MCs are preferably obtained from a subject or an allogeneic donor. The invention also provides a method for producing a population of the invention that is suitable for administration to a subject, wherein the method comprises culturing MCs obtained from the subject under conditions which induce the MCs to differentiate into ioMP cells and (b) harvesting and culturing those progenitor cells which have an expression pattern as defined above and thereby producing a population of the invention that is suitable for administration to the subject. The population will be autologous with the subject and therefore will not be rejected upon implantation. The invention also provides a population of the invention that is suitable for administration to a subject and is produced in this manner.

Alternatively, the invention provides a method for producing a population of the invention that is suitable for administration to a subject, wherein the method comprises culturing MCs obtained from a different subject that is immunologically compatible with the subject into which the cells will be administered under conditions which induce the MCs to differentiate into ioMP cells and (b) harvesting and culturing those ioMP cells which have an expression pattern as defined above and thereby producing a population of the invention that is suitable for administration to the subject. The population will be allogeneic with the subject and therefore will reduce the chance of rejection upon implantation. The invention also provides a population of the invention that is suitable for administration to a subject and is produced in this manner.

In Vitro Methods

The ioMP cells or population of the invention may be used in an in vitro method of regulating the activity of immune cells. The ioMP cells may regulate the activity of any immune cells, such as T cells, B cells, dendritic cells, neutrophils, basophils, mast cells, eosinophils, innate lymphoid cells (ILCs), natural killer (NK) cells, monocytes, macrophages, megakaryocytes, thymocytes or platelets. Preferably, the ioMP cells are used to regulate the activity of T cells. More preferably, the ioMP cells to are used to regulate the activity of helper T (Th) cells, cytotoxic T cells, regulatory T cells (Treg), gamma delta T cells or natural killer T (NKT) cells. Gamma delta T cells are preferred.

Any reference to cytotoxic, helper or gamma delta T cells herein may refer to (i) cytotoxic T cells, (ii) helper T cells, (iii) gamma delta T cells, (iv) cytotoxic T cells and helper T cells, (v) helper T cells and gamma delta T cells, (vi) cytotoxic T cells and gamma delta T cells or (vii) cytotoxic T cells, helper T cells and gamma delta T cells.

The method may comprise incubating the immune cells with a population of the invention under conditions which regulate the activity of the immune cells. For example, the conditions may increase the activity of the immune cells. For instance, the incubation may take place in the presence of lipopolysaccharide. The entire period that the immune cells are incubated with a population of the invention may take place in the present of lipopolysaccharide. Alternatively, only a portion of the period that the immune cells are incubates with a population of the invention make take place in the presence of lipopolysaccharide. In one aspect, the immune cells are incubated with a population of the invention and lipopolysaccharide for a period of one hour.

In another aspect, the conditions may decrease the activity of the immune cells. For instance, the incubation may take place in the presence of poly I:C. The entire period that the immune cells are incubated with a population of the invention may take place in the present of poly I:C. Alternatively, only a portion of the period that the immune cells are incubates with a population of the invention make take place in the presence of poly I:C. In one aspect, the immune cells are incubated with a population of the invention and poly I:C for a period of 24 hours.

In either case, the activity of the immune cells may be evaluated during or after incubation. For instance, the presence or secretion of pro-inflammatory cytokines or other mediators, or a reduction in the presence or secretion of anti-inflammatory cytokines, may indicate that the activity of the immune cells has increased. The presence or secretion of anti-inflammatory cytokines or other mediators, or a reduction in the presence or secretion of pro-inflammatory cytokines, may indicate that the activity of the immune cells has decreased.

Similarly, the phenotype of the population of the invention may be evaluated before, during or after incubation. For instance, the presence or secretion of pro-inflammatory cytokines or other mediators, or a reduction in the presence or secretion of anti-inflammatory cytokines, may indicate that the iOMP cells have a pro-inflammatory phenotype and are primed to increase the activity of the immune cells. The presence or secretion of anti-inflammatory cytokines or other mediators, or a reduction in the presence or secretion of pro-inflammatory cytokines, may indicate that the iOMP cells have an anti-inflammatory phenotype and are primed to decrease the activity of the immune cells The method may further comprise incubating the immune cells with an antigen. The response to be modulated may be a response to the antigen. The response may be antigen-specific.

In particular, the invention provides an in vitro method of increasing the activity of cytotoxic, helper or gamma delta T cells in response to an antigen. Gamma delta T cells are preferred. Techniques for measuring T cell activity are well known in the art. For instance, T cell proliferation and/or cytokine secretion may be measured in response to stimulation (e.g. with the antigen, or with antibodies that bind to the TCR and/or co-stimulatory receptors). Alternatively, activation (e.g. phosphorylation) of proteins downstream of TCR signalling, or gene expression profiling, may give an indication of T cell activation. The method may comprise the step of incubating the T cells with the antigen and a population of the invention. The incubation may be carried out under conditions which increase the activity of the T cells. Such conditions are discussed above and below. The invention also provides primed cytotoxic, helper or gamma delta T cells produced according to this in vitro method. Gamma delta T cells are preferred. Primed T cells are T cells that will robustly respond to an antigen following further contact with the antigen.

The invention also provides an in vitro method of increasing the activity of regulatory T cells in response to an antigen. Methods of measuring T cell activity are discussed above. The method may comprise incubating the T cells with the antigen and a population of the invention. The incubation may be carried out under conditions which increase the activity of the T cells. Such conditions are discussed above and below. The invention further provides primed regulatory T cells produced according to this in vitro method.

In addition, the invention provides an in vitro method of decreasing the activity of cytotoxic, helper or gamma delta T cells in response to an antigen. Gamma delta T cells are preferred. Methods of measuring T cell activity are discussed above. The method may comprise incubating the T cells with the antigen and a population of the invention. The incubation may be carried out under conditions which decrease the activity of the T cells. Such conditions are discussed above and below. The invention further provides suppressed cytotoxic, helper or gamma delta T cells produced according to this in vitro method. Gamma delta T cells are preferred. Suppressed T cells are T cells that subnormally respond to an antigen following further contact with the antigen.

The invention also provides an in vitro method of decreasing the activity of regulatory T cells in response to an antigen. Methods of measuring T cell activity are discussed above. The method may comprise incubating the T cells with the antigen and a population of the invention. The incubation may be carried out under conditions which decrease the activity of the T cells. Such conditions are discussed above and below. The invention further provides suppressed regulatory T cells produced according to this method.

The T cells may be concurrently incubated with the antigen and a population of the invention. On the other hand, the T cells may be incubated with the antigen and the population of the invention separately. For instance, the T cells may be incubated with the antigen and then incubated with the population of the invention. The T cells may be incubated with the population of the invention and then incubated with the antigen. Alternatively, the T cells may be incubated with the antigen to form a T cell/antigen culture. The population of the invention may then be added to the T cell/antigen culture after a period of time has elapsed. Similarly, the T cells may be incubated with the population of the invention to form a T cell/population culture. The antigen may then be added to the T cell/population culture after a period of time has elapsed. The period of time may be anything from 30 seconds to 3 days. For example, the period of time may be 30 seconds, 1 minute, 2 minutes, 5 minutes, 10 minutes, 30 minutes, 1 hour, 2 hours, 4 hours, 8 hours, 12 hours, 1 day, 2 days or 3 days.

The antigen provided to the T cells may be any antigen to which the T cells respond. For example, the antigen may be an antigen that is found on tumour cells. The antigen may also be an antigen found on cells that are present within a healthy or diseased individual. For instance, the antigen may be an one that is associated with autoimmune disease, such as autoimmune encephalomyelitis. The antigen may alternatively be an antigen that is found on a pathogenic agent, such a bacteria, a virus or a protozoa. In some cases, the antigen may be an environmental antigen, such as an allergen. Preferably, the antigen is an antigen that is associated with atopic dermatitis, allergic airway inflammation or perennial allergic rhinitis.

Any of the above in vitro methods may further comprise incubating the T cells with antigen presenting cells. Antigen presenting cells suitable for use in the in vitro methods of the invention include professional antigen presenting cells such as dendritic cells, B cells, macrophages, monocytes, activated epithelial cells, as well as non-professional antigen presenting cells. The T cells are preferably incubated with dendritic cells.

Various culture conditions may be employed to skew the outcome towards an increased T cell response or a decreased T cell response. For example, cytokines, antibodies and/or further antigens may be added to the cell culture. In particular, IL-10 may be added to the cell culture. IL-10 can efficiently enhance immune responses and can skew the outcome towards a stronger Th1 response. Alternatively, Th1 cytokines/mediators such as IL-2, IL-12, IFN-gamma or IgA may be added to skew the immune response towards a Th1 response. Th2 cytokines such as IL-4, IL-5, IL-5, IL-10 or alpha interferon may be added to skew the immune response towards a Th2 response. The oxygen saturation of the culture may be varied. The culture temperature may be varied. The composition of the culture medium may be varied. The culture may be carried out in different vessels.

During the incubation, the ioMPs may influence T cell activity in a variety of ways. For example, there may be interplay or cross-talk between ioMP cell function and T cell function For instance, there may interplay or cross-talk between ioMP cell-mediated inhibition of T-cell function, and T cell cytotoxic attack of ioMP cells. Alternatively, there may be interplay or cross-talk between ioMP cell cytotoxic attach of T cells, and T cell-mediated inhibition of ioMP function. The balance of the interactions may determine whether there is a net increase or net decrease in T cell activation following incubation with ioMP cells.

The ioMP cell-T-cell interaction may involve a positive feedback mechanism. This mechanism may be mediated by interactions between ligands expressed on the ioMP cells and receptors expressed on the T cells, or vice versa. Preferably, the positive feedback mechanism involves the activation of natural killer group 2d (NKG2D) on the T cells. NKG2S is an activating receptor that is found on NK cells and T cells. Its ligands are stress-induced proteins such as MIC-A and MIC-B, both of which are expressed in low amounts on ioMP cells.

The ioMP cells may also be able to alter the T-cell phenotype, and suppress T cell cytokine secretion and cytotoxicity. Indoleamine-pyrrole 2,3-dioxygenase and prostaglandin E2 are thought to be key mediators of ioMP-induced inhibition of T cells.

Furthermore, the micro-environment is of importance for ioMP cell and T cell function, and for the interaction between these cell types. A microenvironment rich in IFN-gamma may protect ioMP cells from being attacked and destroyed by T cells. The ioMP cells may therefore secrete IFN-gamma to promote their own longevity and assist their immuno-modulatory function.

In Vivo Methods

The ioMP cells or population of the invention may be used in an in vivo method of regulating the activity of immune cells. The ioMP cells may regulate the activity of any immune cells, such as T cells, B cells, dendritic cells, neutrophils, basophils, mast cells, eosinophils, innate lymphoid cells (ILCs), natural killer (NK) cells, monocytes, macrophages, megakaryocytes, thymocytes or platelets. Preferably, the ioMP cells are used to regulate the activity of T cells. More preferably, the ioMP cells are used to regulate the activity of helper T (Th) cells, cytotoxic T cells, regulatory T cells (Treg), gamma delta T cells or natural killer T (NKT) cells.

The method may comprise administering a population or pharmaceutical composition of the invention to a subject under conditions which regulate the activity of the immune cells. For example, the conditions may increase the activity of the immune cells. Alternatively, the conditions may decrease the activity of the immune cells.

In particular, the invention provides an in vivo method of increasing the activity of cytotoxic, helper or gamma delta T cells in response to an antigen. Gamma delta T cells are preferred. Methods of measuring T cell activity are discussed above. The method may comprise administering a population or pharmaceutical composition of the invention to a subject. The administration may take place under conditions which increase the activity of the T cells. Such conditions are discussed in more detail below. The invention further provides primed cytotoxic, helper or gamma delta T cells produced according to this method. Gamma delta T cells are preferred. Primed T cells are as defined above.

The invention also provides an in vivo method of increasing the activity of regulatory T cells in response to an antigen. Methods of measuring T cell activity are discussed above. The method may comprise administering a population or pharmaceutical composition of the invention to a subject. The administration may take place under conditions which increase the activity of the T cells. Such conditions are discussed in more detail below. The invention further provides primed regulatory T cells produced according to this method.

In addition, the invention provides an in vivo method of decreasing the activity of cytotoxic, helper or gamma delta T cells in response to an antigen. Gamma delta T cells are preferred. Methods of measuring T cell activity are discussed above. The method may comprise administering a population or pharmaceutical composition of the invention to a subject. The administration may take place under conditions which decrease the activity of the T cells. Such conditions are discussed in more detail below. The invention further provides suppressed cytotoxic, helper or gamma delta T cells produced according to this method. Gamma delta T cells are preferred. Suppressed T cells are as defined above.

The invention also provides an in vivo method of decreasing the activity of regulatory T cells in response to an antigen. Methods of measuring T cell activity are discussed above. The method may comprise administering a population or pharmaceutical composition of the invention to a subject. The administration may take place under conditions which decrease the activity of the T cells. Such conditions are discussed in more detail below. The invention further provides suppressed regulatory T cells produced according to this method.

Any of the above in vivo methods may further comprise administering the antigen to the subject. The antigen may be administered before, at the same time as, or after the population or pharmaceutical composition is administered to the subject. For example, the antigen may be administered the subject from 1 to 28 days, such as 3 to 25 days, 6 to 22 days, 9 to 18 days or 12 to 15 days, before or after the population or pharmaceutical composition is administered. The antigen may be administered the subject 1, 2, 3, 4, 5, 6, 7, 8, 9, 10, 11, 12, 13, 14, 15, 16, 17, 18, 19, 20, 21, 22, 23, 24, 25, 26, 27 or 28 days before or after the population or pharmaceutical composition is administered.

The antigen may be administered to the subject on one occasion. Alternatively, the antigen may be administered to the subject on at least two occasions, such as at least 3, at least 4, at least 5, at least 6, at least 7, at least 8, at least 9 or at least 10 occasions. The interval between the occasions may be from 1 to 28 days, such as 3 to 25 days, 6 to 22 days, 9 to 18 days or 12 to 15 days. Preferably, the interval between occasions is 1, 2, 3, 4, 5, 6, 7, 8, 9, 10, 11, 12, 13, 14, 15, 16, 17, 18, 19, 20, 21, 22, 23, 24, 25, 26, 27 or 28 days.

Similarly, the ioMP cells may be administered to the subject on one occasion. Alternatively, the ioMP cells may be administered to the subject on at least two occasions, such as at least 3, at least 4, at least 5, at least 6, at least 7, at least 8, at least 9 or at least 10 occasions. The interval between the occasions may be from 1 to 28 days, such as 3 to 25 days, 6 to 22 days, 9 to 18 days or 12 to 15 days. Preferably, the interval between occasions is 1, 2, 3, 4, 5, 6, 7, 8, 9, 10, 11, 12, 13, 14, 15, 16, 17, 18, 19, 20, 21, 22, 23, 24, 25, 26, 27 or 28 days.

An adjuvant may be administered to the individual before, at the same time as, or after the antigen. Suitable adjuvants are known in the art. These include but are not limited to alum, aluminum hydroxide, aluminum phosphate, calcium phosphate hydroxide, paraffin oil, killed *Bordetella pertussis, Mycobacterium bovis*, bacterial toxoids, squalene, thimerosal, detergents, plant saponins such as those from *Quillaja*, Soybean and *Polygala senega*, cytokines such as IL-1, IL-2 and IL-12, Freund's complete adjuvant and Freund's incomplete adjuvant.

The antigen may be any antigen to which the T cells respond. For example, the antigen may be an antigen that is found on tumour cells. Alternatively, the antigen may be an one that is associated with autoimmune disease, such as autoimmune encephalomyelitis. The antigen may also be an antigen that is found on the subject's own cells. In contrast, the antigen may be an antigen that is found on the cells of another healthy or diseased individual. In some instances, the antigen is one that is found on the cells of another individual but that is not found on the subject's own cells. The antigen may alternatively be an antigen that is found on a pathogenic agent, such a bacteria, a virus or a protozoa. In some instances, the antigen may be an environmental antigen, such as an allergen. Preferably, the antigen is an antigen that is associated with atopic dermatitis, allergic airway inflammation or perennial allergic rhinitis.

The outcome of administration of the population of the invention (i.e. increased or decreased T cell responses) is dependent on the conditions under which the population of the invention is administered. Such conditions may pre-exist in the subject. The conditions may naturally exist in the healthy state. Alternatively, the conditions may be associated with disease in the subject. Ins some cases, the conditions may be induced in the subject prior to, concurrently with, or after administration of the population. The conditions may be induced by administering one or more substances to the subject. Such substances may include drugs, vaccines, antibodies, antigens, adjuvants, cytokines, nucleic acids, peptides, proteins and cells.

For instance, a Th1 and/or Th2 immune response may pre-exist in the subject or be induced in the subject. Th1 responses may be enhanced by cytokines/mediators such as IL-2, IL-12, IFN-gamma, and IgA (an immunoglobulin that supports mucosal immunity). Th2 immune responses may be enhanced by IL4, IL-5, IL-6 and IL-10. Accordingly, one or more of these cytokines/mediators may be present in the subject prior to administration of the population. One or more of these cytokines/mediators may be administered to the subject prior to, concurrently with, or after administration of the population.

In one aspect, administration of the population of the invention affects the Th1/Th2 balance in the subject. A failure of the Th1 arm of the immune system and an overactive Th2 arm is implicated in a wide variety of chronic illnesses. These include acquired immune deficiency syndrome (AIDS), chronic fatigue immune dysfunction (CFIDS), Candidiasis, allergies, Multiple Chemical Sensitivities (MCS), viral hepatitis, Gulf War Syndrome (GWS), cancer, etc. In AIDS, for instance, it has been reported that as HIV infection progresses from the asymptomatic stage to advanced disease, the immune response shifts from a more effective Th1 response to an ineffective Th2 response. Accordingly, restoring the balance between the Th1 and Th2 arms of the immune system by stimulating Th1 responses and decreasing Th2 responses may diminish or ablate many of the symptoms associated with the chronic illnesses set out above.

Mechanisms by which ioMP cells may modulate T cell activity are discussed above.

Pharmaceutical Compositions and Administration

The invention additionally provides a pharmaceutical composition comprising an ioMP cell of the invention or a population of the invention in combination with a (i) pharmaceutically acceptable carrier or diluent, (ii) one or more lipsomes and/or (iii) one or more microbubbles. The composition may comprise (i); (ii); (iii); (i) and (ii); (i) and (iii); (ii) and (iii); or (i), (ii) and (iii). The ioMP cell or population are preferably contained with the one or more liposomes and/or one or more microbubbles. Any number of liposomes and/or microbubbles may be present. Any of the numbers discussed above with reference to the population of the invention are equally application to the lipsomes and/or microbubbles. A lipsome or microbubble may contain one ioMP cell or more than one ioMP cell.

The invention also provides a pharmaceutical composition comprising (i) an IMP cell of the invention or a population of the invention in combination with a pharmaceutically acceptable carrier or diluent, (ii) one or more immune cells and/or (iii) one or more antigens. The composition may comprise (i); (ii); (iii); (i) and (ii); (i) and (iii); (ii) and (iii); or (i), (ii) and (iii). The immune cell may be any immune cell, such as those discussed above. In some aspects, the immune cell may be a T-cell, a gamma delta T-cell or an NK cell. The antigen may be any antigen, such as any of the antigens discussed above.

The various compositions of the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19$^{th}$ Edition, Mack Publishing Company, Eastern Pennsylvania, USA.

The cells may be administered by any route. Suitable routes include, but are not limited to, intravenous, intramuscular, subcutaneous, intraperitoneal, endomyocardial, epimyocardial, intraventicular, intracoronary, retrograde coronary sinus, intra-arterial, intra-pericardial, intraosseous, or intra-pulmonary route. The cells may also be administered directly to a tissue of interest, such as liver, kidney or lung tissue. The cells may be administered directly into a tumour.

Compositions may be prepared together with a physiologically acceptable carrier or diluent. Typically, such compositions are prepared as liquid suspensions of cells. The cells may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions of the invention may contain minor amounts of auxiliary substances such as wetting or emulsifying agents, pH buffering agents, and/or adjuvants which enhance effectiveness. The composition preferably comprises human serum albumin.

One suitable carrier or diluents is Plasma-Lyte A®. This is a sterile, nonpyrogenic isotonic solution for intravenous administration. Each 100 mL contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2.3H_2O$); 37 mg of Potassium Chloride, USP (KCl); and 30 mg of Magnesium Chloride, USP ($MgCl_2.6H_2O$). It contains no antimicrobial agents. The pH is adjusted with sodium hydroxide. The pH is 7.4 (6.5 to 8.0).

The ioMP cells may be contained within one or more liposomes and/or one or more microbubbles. Suitable liposomes are known in the art. Suitable liposomes are disclosed in, for example, Akbarzadeh et al. Nanoscale Research Letters 2013, 8:102 and Meghana et al. International Journal Of Pharmaceutical And Chemical Sciences, 2012, 1(1): 1-10. Suitable lipids for use in forming liposomes are discussed below with reference to microbubbles.

Microbubbles, their formation and biomedical uses are known in the art (e.g. Sirsi and Borden, Bubble Sci Eng Technol. November 2009; 1(1-2): 3-17). Microbubbles are bubbles smaller than one millimeter in diameter and larger than one micrometer in diameter. The microbubble used in the present invention is preferably 8 µm or less in diameter, such as 7 µm or less in diameter, 6 µm or less in diameter, 5 µm or less in diameter, 4 µm or less in diameter, 3 µm or less in diameter or 2 µm or less in diameter.

The microbubble may be formed from any substance. The general composition of a microbubble is a gas core stabilised by a shell. The gas core may comprise air or a heavy gas, such as perfluorocarbon, nitrogen or perflouropropane. Heavy gases are less water soluble and so are less likely to leak out from the microbubble leading to microbubble dissolution. Microbubbles with heavy gas cores typically last longer in circulation.

The shell may be formed from any material. The shell material preferably comprises a protein, a surfactant, a lipid, a polymer or a mixture thereof.

Suitable proteins, include but are not limited to, albumin, lysozyme and avidin. Proteins within the shell may be chemically-crosslinked, for instance by cysteine-cysteine linkage. Other crosslinkages are known in the art.

Suitable surfactants include, but are not limited to, sorbitan monopalmitate (such as SPAN-40), polysorbate detergents (such as TWEEN-40), mixtures of SPAN-40 and TWEEN-40 and sucrose stearate (mono- and di-ester).

Suitable polymers include, but are not limited to, alginate polymers, double ester polymers of ethylidene, the copolymer poly(D,L-lactide-co-glycolide) (PLGA), poly(vinyl alcohol) (PVA), the copolymer polyperfluorooctyloxycaronyl-poly(lactic acid) (PLA-PFO) and other block copolymers. Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles.

The copolymer may be a triblock, tetrablock or pentablock copolymer. Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Any lipid material that forms a microbubble may be used. The lipid composition is chosen such that the microbubble has the required properties, such surface charge, packing density or mechanical properties. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipid typically comprises a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the ligands, receptors ro antibodies as discussed above.

The lipid composition may comprise one or more additives that will affect the properties of the microbubble. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

The microbubble shell is preferably formed from a phospholipid. Suitable phospholipids are known in the art.

There are several commercially available lipid shell microbubble formulations such as Definity (Lantheus Medical Imaging) and Sonovue® (Bracco Diagnostics).

The microbubble may also be formed from a polymer-surfactant hybrid that involves forming polyelectrolyte multilayer (PEM) shells on a preformed microbubble. The preformed microbubble is coated with a charged surfactant or protein layer, which serves as a substrate for PEM deposition. The layer-by-layer assembly technique is used to sequentially adsorb oppositely charged polyions to the microbubble shell. For instance, PEM can be deposited onto microbubbles using poly(allylamine hydrochloride) (PAH) and poly(styrene sulfonate) (PSS) for the polyion pair. PEM microbubbles with phospholipid containing the cationic headgroup trimethylammonium propane (TAP) as the underlying shell and DNA and poly(L-lysine) (PLL) as the polyion pair have also been developed.

The microbubble is typically formed by providing an interface between a gas and a microbubble shell material. Any of the materials discussed above may be used. Some materials, such as phospholipids, spontaneously form microbubbles. Phospholipids self assemble into a microbubble. Other materials require sonication of the interface, i.e. the application of sound energy or sonic waves to the interface. Ultrasonic waves are typically used. Suitable methods are known in the art for sonication.

The microbubble may be loaded with the ioMP cells after formation of the microbubble or during formation of the microbubble.

The ioMP cells are administered in a manner compatible with the dosage formulation and in such amount will be therapeutically effective. The quantity to be administered depends on the subject to be treated, capacity of the subject's immune system and the degree repair desired. Precise amounts of ioMP cells required to be administered may depend on the judgment of the practitioner and may be peculiar to each subject.

Any suitable number of cells may be administered to a subject. For example, at least, or about, $0.2 \times 10^6$, $0.25 \times 10^6$, $0.5 \times 10^6$, $1.5 \times 10^6$, $4.0 \times 10^6$ or $5.0 \times 10^6$ cells per kg of subject may administered. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Typically, up to $2 \times 10^8$ ioMP cells are administered to each subject. Any of the specific numbers discussed above with reference to the populations of the invention may be administered. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration.

Medicaments, Methods and Therapeutic Use

The ioMP cells of the invention may be used in a method of therapy of the human or animal body. Thus the invention provides an ioMP cell of the invention, a population of the invention, or a pharmaceutical composition of the invention for use in a method of treatment of the human or animal body by therapy. In particular, the invention concerns using the ioMP cells of the invention, a population of the invention, or the pharmaceutical composition of the invention to treat disease by modulating immune cell responses. The immune cells are preferably T cells. The invention also concerns using the ioMP cells of the invention, a population of the invention or the pharmaceutical composition of the invention to treat cancer in a subject. The invention further concerns using the ioMP cells of the invention, a population of the invention or the pharmaceutical composition of the invention to treat an allergic or autoimmune disease in a subject.

More specifically, the invention provides a method of treating a disease by increasing cytotoxic, helper or gamma delta T cell responses to an antigen in a subject, the method comprising administering to the subject: (a) the population of the invention or the pharmaceutical composition of the invention; (b) the population of the invention or the pharmaceutical composition of the invention, and the primed cytotoxic, helper or gamma delta T cells of the invention; or (c) the primed cytotoxic, helper or gamma delta T cells of the invention. Gamma delta T cells are preferred.

The invention also provides a method of treating a disease by decreasing regulatory T cell responses to an antigen in a subject, the method comprising administering to the subject: (a) the population of the invention or the pharmaceutical composition of the invention; (b) the population of the invention or the pharmaceutical composition of the invention and the suppressed regulatory T cells of the invention; or (c) the suppressed regulatory T cells of the invention.

The invention further provides a method of treating a disease by decreasing regulatory T cell responses to an antigen in a subject, the method comprising administering to the subject: (a) the population of the invention or the pharmaceutical composition of the invention and the primed cytotoxic, helper or gamma delta T cells of the invention; or (b) the primed cytotoxic, helper or gamma delta T cells of the invention. Gamma delta T cells are preferred.

The disease may be any disease in which the subject may benefit from increased cytotoxic, helper T or gamma delta T cell responses or decreased regulatory T cell response to an antigen. The disease is preferably cancer. Preferably, the cancer is anal cancer, bile duct cancer (cholangiocarcinoma), bladder cancer, blood cancer, bone cancer, bowel cancer, brain tumours, breast cancer, colorectal cancer, cervical cancer, endocrine tumours, eye cancer (such as ocular melanoma), fallopian tube cancer, gall bladder cancer, head and/or neck cancer, Kaposi's sarcoma, kidney cancer, larynx cancer, leukaemia, liver cancer, lung cancer, lymph node cancer, lymphoma, melanoma, mesothelioma, myeloma, neuroendocrine tumours, ovarian cancer, oesophageal cancer, pancreatic cancer, penis cancer, primary peritoneal cancer, prostate cancer, *Pseudomyxoma peritonei*, skin cancer, small bowel cancer, soft tissue sarcoma, spinal cord tumours, stomach cancer, testicular cancer, thymus cancer, thyroid cancer, trachea cancer, unknown primary cancer, vagina cancer, vulva cancer or endometrial cancer. The leukaemia is preferably acute lymphoblastic leukaemia, acute myeloid leukaemia, chronic lymphocytic leukaemia or chronic myeloid leukaemia. The lymphoma is preferably Hodgkin lymphoma or non-Hodgkin lymphoma. The cancer is preferably primary cancer or secondary cancer.

The invention also provides a method of treating cancer in a subject, the method comprising administering to the subject a population of the invention or the pharmaceutical composition of the invention. The cancer is preferably a cancer that is mentioned above with reference to treating a disease by regulating T cell responses.

In another aspect, the invention provides a method of treating a disease by decreasing cytotoxic and/or helper T cell responses to an antigen in a subject, the method comprising administering to the subject: (a) the population of the invention or the pharmaceutical composition of the invention; (b) the population of the invention or the pharmaceutical composition of the invention and the suppressed cytotoxic, helper or gamma delta T cells of the invention; or (c) the suppressed cytotoxic, helper or gamma delta T cells of the invention. Gamma delta T cells are preferred.

The invention also provides a method of treating a disease by increasing regulatory T cell responses to an antigen in a subject, the method comprising administering to the subject: (a) the population of the invention or the pharmaceutical composition of the invention; (b) the population of the invention or the pharmaceutical composition of the invention, and the primed regulatory T cells of the invention; or (c) the primed regulatory T cells of the invention.

The invention further provides a method of treating a disease by decreasing cytotoxic, helper or gamma delta T cell responses to an antigen in a subject, the method comprising administering to the subject: (a) the population of the invention or the pharmaceutical composition of the invention and the primed regulatory T cells of the invention; or (b) the primed regulatory T cells according to of the invention. Gamma delta T cells are preferred.

The disease may be any disease in which the subject may benefit from decreased cytotoxic, helper or gamma delta T cell responses or increased regulatory T cell responses to an antigen. Gamma delta T cells are preferred. In some instances, the disease is preferably an allergic disease. More preferably, the disease is atopic dermatitis, allergic airway inflammation or perennial allergic rhinitis.

In other instances, the disease is preferably an autoimmune disease. For example, the disease may be alopecia areata, autoimmune encephalomyelitis, autoimmune hemolytic anemia, autoimmune hepatitis, dermatomyositis, diabetes (type 1), autoimmune juvenile idiopathic arthritis, glomerulonephritis, Graves' disease, Guillain-Barré syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, autoimmune thyroiditis, uveitis or vitiligo. The disease is preferably autoimmune encephalomyelitis. In other cases, the disease is preferably an immune-mediated disease. The disease is more preferably graft versus host disease (GVHD).

In a further aspect, the invention provides a method of treating an allergic, autoimmune or immune-mediated disease in a subject, the method comprising administering to the subject the population of the invention or the pharmaceutical composition of the invention. The allergic, autoimmune or immune-mediated disease is preferably a disease that is mentioned above with reference to treating a disease by regulating T cell responses.

For any of the above methods, the antigen may be any antigen to which the T cells respond. For example, the antigen may be an antigen that is found on tumour cells. Alternatively, the antigen may be an one that is associated with autoimmune disease, such as autoimmune encephalomyelitis.

The antigen may also be an antigen that is found on the subject's own cells. In contrast, the antigen may be an antigen that is found on the cells of another healthy or diseased individual. In some instances, the antigen is one that is found on the cells of another individual but that is not found on the subject's own cells. The antigen may alternatively be an antigen that is found on a pathogenic agent, such a bacteria, a virus or a protozoa. In some instances, the antigen may be an environmental antigen, such as an allergen. Preferably, the antigen is an antigen that is associated with atopic dermatitis, allergic airway inflammation or perennial allergic rhinitis.

As set out above, the method may involve administering the T cells of the invention to the subject. The T cells are preferably autologous or allogeneic. The T cells are preferably chimeric antigen receptor (CAR) T cells. CAR T cells are described in more detail below. The number of T cells administered to the subject is preferably a therapeutically effective number. For example, $0.2\times10^6$, $0.25\times10^6$, $0.5\times10^6$, $1.5\times10^6$, $4.0\times10^6$ or $5.0\times10^6$ T cells per kg of subject may be administered. For example, at least, or about, $10^5$, $10^6$, $10^7$, $10^8$, $10^9$ T cells may be administered. As a guide, the number of T cells to be administered may be from $10^5$ to $10^9$, preferably from $10^6$ to $10^8$. Typically, up to $2\times10^8$ T cells are administered to each subject.

The method may also involve administering both (i) the population of the invention or the pharmaceutical composition of the invention, and (ii) the T cells of the invention to the subject. In such cases, the population or pharmaceutical composition of the invention may be administered simultaneously, sequentially or separately with the T cells of the invention. The population or pharmaceutical composition of the invention may be administered before or after the T cells of the invention. For example, the population or pharmaceutical composition of the invention may be administered the subject from 1 to 28 days, such as 3 to 25 days, 6 to 22 days, 9 to 18 days or 12 to 15 days, before or after the T cells of the invention are administered. The population or pharmaceutical composition of the invention may be administered the subject up to 1, up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27 or up to 28 days before or after the T cells of the invention are administered.

The population of the invention and/or the pharmaceutical composition of the invention and/or the T cells of the invention may be administered to the subject on one occasion. Alternatively, the population of the invention and/or the pharmaceutical composition of the invention and/or the T cells of the invention n may be administered to the subject on at least two occasions, such as at least 3, at least 4, at least 5, at least 6, at least 7, at least 8, at least 9 or at least 10 occasions. The interval between the occasions may be from 1 to 28 days, such as 3 to 25 days, 6 to 22 days, 9 to 18 days or 12 to 15 days. Preferably, the interval between occasions is 1, 2, 3, 4, 5, 6, 7, 8, 9, 10, 11, 12, 13, 14, 15, 16, 17, 18, 19, 20, 21, 22, 23, 24, 25, 26, 27 or 28 days.

In any of the therapeutic methods set out above, the ioMP cells may secrete cytokines. The ioMP cells preferably secrete pro-inflammatory cytokines or anti-inflammatory cytokines. Secretion of cytokines by ioMP cells is discussed in more detail above. The ioMP cells may also secrete molecules that regulate apoptosis. Preferably, the ioMP cells secrete pro-apoptotic or anti-apoptotic molecules.

For instance, the ioMP cells may secrete or express pro-apoptotic molecules such as Notch2, cadherin 11 (CDH11), CD81, CD95, CD230, CD295, CD55, CD82, LBTR, beta 2-microglubulin and/or DR6. Notch2 signalling is known to induce apoptosis. CD82, CD95, CD230, CD81 and beta 2-microglubulin are also known to induce apoptosis. Enhanced CD295 expression marks apoptotic cells. LTBR activates multiple signalling pathways leading to the expression of adhesion molecules and chemokines, and cell death. DR6 is also known as CD358 or TNFRSF21, and is a member of the umour necrosis factor receptor superfamily. DR6 activates nuclear factor kappa-B and mitogen-activated protein kinase 8 and induces cell apoptosis.

The ioMP cells may secrete anti-apoptotic molecules such as CD66e (CEACAM-5), CD264, CD63, CD120a and/or CD105. CD66e promotes tumour cell migration, invasion, adhesion, and metastasis, and contributes to tumour formation by maintaining cellular proliferation in the presence of differentiation stimuli and by blocking apoptosis following loss of ECM anchorage. CD264 has been shown to play an inhibitory role in TNF-related apoptosis-inducing ligand (TRAIL)-induced cell apoptosis. CD63 is bound by TIMP-1, leading to activation of intracellular signal transduction pathways and inhibition of apoptosis. CD120a is phosphorylated to recruit Bcl-2 and protect against apoptosis.

The iOMP cells may secrete or express other molecules that regulate apoptosis, such as CD44 and/or CD59. CD59 has been shown to regulate apoptosis of human lung cancer cells.

The ioMP cells preferably target cells by contact-dependent cell lysis. In particular, the ioMP cells may attack tumour cells by contact-dependent cell lysis. Mechanisms of ioMP action are discussed in more detail above.

In all instances, the ioMP cells are preferably derived from the subject or an allogeneic donor. Deriving the ioIMP cells of the invention from the subject should ensure that the ioMP cells are themselves not rejected by the subject's immune system. Any difference between the donor and recipient will ultimately cause clearance of the ioMP cells, but not before they have modulated the relevant T cell responses and/or at least partially treated the disease.

The invention concerns administering to the subject a therapeutically effective number of ioMP cells of the invention to the subject. A therapeutically effective number is a number which ameliorates one or more symptoms of the disease. A therapeutically effective number is preferably a number which treats the disease. Suitable numbers of ioMP cells are discussed in more detail above.

The ioMP cells of the invention may be administered to any suitable subject. The subject is generally a human subject. The subject may be any of the animals or mammals mentioned above with reference to the source of the ioMP cells.

The subject may be an infant, a juvenile or an adult. The subject may be known to have a disease or is suspected of having a disease. The subject may be susceptible to, or at risk from, the relevant disease. For instance, the subject may be genetically predisposed to cancer or autoimmune disease.

The invention may be used in combination with other means of, and substances for, treating disease. In some cases, the ioMP cells of the invention may be administered simultaneously, sequentially or separately with other substances which are intended for treating the disease or ameliorating the symptoms of the disease, or for providing pain relief. The ioMP cells may be used in combination with existing treatments for disease and may, for example, be simply mixed with such treatments. Thus the invention may be used to increase the efficacy of existing treatments for disease.

Chimeric Antigen Receptor (CAR) T Cells

T cells play a key role in many immune responses. In particular, T cells are important for cell-mediated immunity to cancer cells. Cancer cells use many strategies to evade the host immune response. For example, cancer cells may downregulate antigens that are targeted by T cells, or may express antigens that are only weakly immunogenic. In addition, many tumours create a immunosuppressive microenvironment that is not conducive to effective T cell responses.

T cells can be genetically modified in order to increase their anti-tumour responses, thereby enhancing tumour immunity. For example, a T cell can be induced to express a chimeric antigen receptor (CAR) specific for an antigen present on cancer cells. In this way, the T cell becomes specific for a key tumour antigen. This ensures that the T cell's responses are efficiently targeted towards the cancer.

In more detail, a CAR typically comprises an antigen-binding region, a transmembrane domain, and at least one intracellular domain. The antigen-binding region confers the specificity of the CAR and is often derived from an antibody. As antibodies to many targets are known, CARs specific for almost any antigen can be engineered. The transmembrane domain anchors the CAR to the T cell. The intracellular domain induces T cell signalling, leading to activation, persistence and effector function.

Normally, T cell activation requires the T cell to interact with an antigen presenting cell. Specifically, the T cell receptor (TCR) recognises a peptide antigen associated with MHC molecule present on the antigen presenting cell. This means that traditional T cell activation relies on antigen uptake, processing and presentation by antigen presenting cells.

In contrast, CAR-expressing T cells (CAR T cells) can be activated in the absence of an interaction with an MHC molecule. When the antigen-binding region binds to the target antigen, signalling events are triggered via the CAR intracellular domain(s) and the CAR T cell becomes activated. This circumvention of MHC-restriction means that the CAR T cell approach can be used to broaden the applicability of adoptive T-cell therapy. Moreover, CAR T cells may recognise antigens other than proteins or peptides. In particular, CARs may recognise carbohydrate and glycolipid structures that are typically expressed on the surface of cancer cells. CARs can therefore redirect the effector functions of a T cell towards any protein or non-protein target expressed on the cell surface as long as an antibody or similar targeting domain is available.

CAR T cells are produced by inducing CAR expression in T cells isolated from a subject. Specifically, T cells can be isolated from blood or other tissues and modified to express CARs. CAR T cells produced in this way are generally administered autologously. In other words, the resultant CAR T cells are administered to the same subject as that from which they were derived. However, the ability to administer allogeneic CAR T cells (i.e. CAR T cells that are derived from a subject that is immunologically compatible with the subject into which the cells are administered) would be advantageous. For example, a bank of CAR T cells directed to particular antigens could be generated and maintained for use in the treatment of an array of MHC-mismatched subjects. In practice, allogeneic CAR T cells are less stable and therefore less viable than autologous CAR T cells. Allogeneic CAR T cell administration is therefore challenging.

To address this issue, the present invention provides a method of improving the potency, viability or stability of CAR T cells, comprising incubating CAR T cells in the presence of a population of the invention. The method of the invention gives rise to CART cells with improved persistence and function, which may be therefore be administered autologously or allogeneically. Furthermore, the more stable phenotype increases the efficacy of the CART cells and reduces off-target effects. In other words, the CAR T cells produced according to the method of the invention remain more specifically targeted to the relevant antigen and are thus safer for use in vivo.

The method of the invention may improve the in vitro and/or in vivo potency, viability or stability of the CART cells. Methods for evaluating T cell potency, viability and stability are well known in the art.

Incubation of the CAR T cells with the population of the invention may comprise contacting the CAR T cells with the population. For instance, the CAR T cells may be contacted with the population for at least 1 minute, at least 2 minutes, at least 5 minutes, at least 10 minutes, at least 20 minutes, at least 30 minutes, at least 1 hours, at least 2 hours, at least 4 hours, or at least 8 hours. Incubation of the CART cells with the population of the invention may also comprise co-culture of the CAR T cells with the population. For example, the CAR T cells and the population may be co-cultured for at least 12 hours, at least 24 hours, at least 48 hours, at least 72 hours or at least 96 hours. Techniques for culturing cells are well known in the art. The cells are may be cultured under standard conditions of 37° C., 5% $CO_2$ in medium without serum. The cells may be cultured in any suitable flask or vessel, including wells of a flat plate such as a standard 6 well plate. Such plates are commercially available from Fisher scientific, VWR suppliers, Nunc, Starstedt or Falcon. The wells typically have a capacity of from about 1 ml to about 4 ml.

The flask, vessel or wells within which the population is contained or cultured may be modified to facilitate handling of the cells. For instance, the flask, vessel or wells may be modified to facilitate culture of the cells, for instance by including a growth matrix. The flask, vessel or wells may be modified to allow attachment of the cells or to allow immobilization of the cells onto a surface. One or more surfaces may be coated with extracellular matrix proteins such as laminin or collagen or any other capture molecules that bind to the cells and immobilize or capture them on the surface(s).

Other substances may be provided to the CAR T cells and the population of the invention during the incubation period. In particular, the incubation may take place in the presence of antigen presenting cells, T cell activator beads, or one or more antibodies. The antigen presenting cell are preferably dendritic cells. The antibodies are preferably anti-CD3 and/or anti-CD28. The incubation may also take place in the presence of an antigen. The antigen is preferably the antigen for which the CAR T cells are specific. Other substances that may be provided during the incubation step are cytokines, nucleic acids, peptides, proteins and other types of cells.

Hybrid Composition

One or more ioMP cells of the invention may form part of a hybrid composition as disclosed in PCT/GB2015/051672 and are preferably administered to a subject as part of such a composition. In particular, the invention provides a hybrid composition, which comprises:

(a) one or more biocompatible fibres;
(b) one or more ioMP cells of the invention; and
(c) one or more biocompatible components which (i) attach the one or more ioMP cells to the one or more fibres and/or embed the one or more ioMP cells and the one or more fibres and/or (ii) are capable of attaching the composition to a tissue.

The hybrid composition of the invention comprises one or more biocompatible fibres. A fibre is biocompatible if it does not cause any adverse reactions or side effects when contacted with a damaged tissue.

Any number of biocompatible fibres may be present in the composition. The composition may comprise only one fibre. The composition typically comprises more than one fibre, such at least 2, at least 5, at least 10, at least 20, at least 30, at least 40, at least 50, at least 100, at least 200, at least 500 fibres, at least 1000 fibres or even more fibres.

Suitable biocompatible fibres are known in the art. The one or more biocompatible fibres may be natural or synthetic. Preferred biocompatible fibres include, but are not limited to, cellulose fibres, collagen fibres, collagen-glycosaminoglycan fibres, gelatin fibres, silk fibroin fibres, one or more fibrin fibres, chitosan fibres, starch fibres, alginate fibres, hyaluronan fibres, poloaxmer fibres or a combination thereof. The glycosaminoglycan is preferably chondroitin. The cellulose is preferably carboxymethylcellulose, hydroxypropylmethylcellulose or methylcellulose. The poloaxmer is preferably pluronic acid, optionally Pluronic F-127.

If more than one fibre is present in the composition, the population of fibres may be homogenous. In other words, all of the fibres in the population may be the same type of fibre, e.g. cellulose fibres. Alternatively, the population of fibres may be heterogeneous. In other words, the population of fibres may contain different types of fibre, such cellulose fibres and collagen fibres.

The one or more fibres may be any length. The one or more fibres are preferably approximately the same length as the depth of the damage in the tissue which is to be treated using the composition. The length of one or more fibres is preferably designed such that the composition can penetrate a damaged tissue to a prescribed depth. The one or more fibres may be any length. The lower limit of the length of the one or more fibres is typically determined by the diameter of the one or more therapeutic cells. Suitable lengths include, but are not limited to, at least 1 µm in length, at least 10 µm in length, at least 100 µm in length, at least 500 µm in length, at least 1 mm in length, at least 10 mm (1 cm) in length, at least 100 mm (10 cm) in length, at least 500 mm (50 cm) in length or at least 1000 mm (100 cm or 1 m) in length. The one or more fibres may be even longer. For instance, the one or more fibres may be up to 5 m or 10 m in length, for instance if being used to repair damage along the human intestinal tract, or even longer if being used in larger animals, such as horses. The length of the one or more fibres is typically determined by their intended use and/or their ability to be manipulated, for instance by a surgeon, by a robot or via some other means, such as magnetically.

The one or more fibres may be charged. The one or more fibres are preferably positively-charged. The one or more fibres are preferably negatively-charged.

The one or more fibres may be magnetic. The one or more fibres may be modified to include one or more magnetic atoms or groups. This allows magnetic targeting of the composition. The magnetic atoms or groups may be paramagnetic or superparamagnetic. Suitable atoms or groups include, but are not limited to, gold atoms, iron atoms, cobalt atoms, nickel atoms and a metal chelating groups, such as nitrilotriacetic acid, containing any of these atoms. The metal chelating group may, for instance, comprise a group selected from —C(=O)O—, —C—O—C—, —C(=O), —NH—, —C(=O)—NH, —C(=O)—CH$_2$-I, —S(=O)$_2$— and —S—.

The composition also comprises one or more biocompatible components. The one or more biocompatible components (i) attach the one or more ioMP cells to the one or more fibres and/or embed the one or more ioMP cells and the one or more fibres and/or (ii) are capable of attaching the composition to a tissue. The one or more biocompatible components may (a) attach the one or more ioMP cells to the one or more fibres, (b) embed the one or more ioMP cells and the one or more fibres, (c) be capable of attaching the composition to a tissue, (d) attach the one or more ioMP cells to the one or more fibres and embed the one or more ioMP cells and the one or more fibres, (e) attach the one or more ioMP cells to the one or more fibres and be capable of attaching the composition to a tissue, (f) embed the one or more ioMP cells and the one or more fibres and be capable of attaching the composition to a tissue or (g) attach the one or more ioMP cells to the one or more fibres, embed the one or more ioMP cells and the one or more fibres and be capable of attaching the composition to a tissue.

A component is biocompatible if it does not cause any adverse reactions or side effects when contacted with a damaged tissue.

Any number of biocompatible components may be present in the composition. The composition typically comprises only one component or two components. The composition may comprise more than two components, such as at least 3, at least 5, at least 10, at least 20, at least 30, at least 40, at least 50 components or even more components.

The one or more biocompatible components preferably comprise a biocompatible adhesive which attaches the one or more therapeutic cells to the one or more fibres. The biocompatible adhesive may attach the one or more ioMP cells (a) on the surface of the one or more fibres, (b) within the one or more fibres or (c) both on the surface of and within the one or more fibres.

The biocompatible adhesive may be natural or synthetic. Suitable biocompatible adhesives are known in the art. Suitable adhesives include, but are not limited to, fibrin, fibrin gel, integrin, integrin gel, cadherin and cadherin gel.

The one or more biocompatible components preferably comprise a biocompatible gel which embeds the one or more therapeutic cells and the one or more fibres. Suitable biocompatible gels are known in the art. The biocompatible gel may be natural or synthetic. Preferred biocompatible gels include, but are not limited to, a cellulose gel, a collagen gel, a gelatin gel, a fibrin gel, a chitosan gel, a starch gel, an alginate gel, a hyaluronan gel, an agarose gel, a poloaxmer gel or a combination thereof.

The cellulose gel may be formed from any of the celluloses discussed above. The cellulose polymer concentration is preferably from about 1.5% (w/w) to about 4.0% (w/w), such as from about 2.0% (w/w) to about 3.0% (w/w). The cellulose polymer preferably has a molecular weight of from about 450,000 to about 4,000,000, such as from about 500,000 to about 3,500,000, from about 500,000 to about 3,000,000 or from about 750,000 to about 2,500,000 or from about 1000,000 to about 2,000,000.

The poloaxmer gel is preferably a pluronic acid gel, optionally a Pluronic F-127 gel.

The adhesive and/or gel preferably has a viscosity in the range of 1000 to 500,000 mPa·s (cps) at room temperature, such as from about 1500 to about 450,000 mPa·s at room temperature, from about 2000 to about 400,000 mPa·s at room temperature, from about 2500 to about 350,000 mPa·s at room temperature, from about 5000 to about 300,000 mPa·s at room temperature, from about 10,000 to about 250,000 mPa·s at room temperature, from about 50,000 to about 200,000 mPa·s at room temperature or from about 50,000 to about 150,000 mPa·s at room temperature.

Viscosity is a measure of the resistance of the adhesive and/or gel to being deformed by either shear stress or tensile stress. Viscosity can be measured using any method known in the art. Suitable methods include, but are not limited to, using a viscometer or a rheometer.

Room temperature is typically from about 18° C. to about 25° C., such as from about 19° C. to about 24° C. or from about 20° C. to about 23° C. or from about 21° C. to about 22° C. Room temperature is preferably any of 18° C., 19° C., 20° C., 21° C., 22° C., 23° C., 24° C. and 25° C. Viscosity is most preferably measured at 25° C.

The one or more biocompatible components preferably comprises a biocompatible adhesive which attaches the one or more therapeutic cells to the one or more fibres and a biocompatible gel which embeds the one or more therapeutic cells and the one or more fibres. For instance, the composition may comprise a fibrin gel which attaches the one or more ioMP cells to the one or more fibres and a cellulose gel which embeds the one or more ioMP cells and the one or more fibres.

In any of the embodiments discussed above, the biocompatible adhesive and/or the biocompatible gel preferably comprises platelet lysate. For instance, the adhesive and/or the gel may be a platelet lystae gel. Platelet lysate refers to the combination of natural growth factors contained in platelets that has been released through lysing those platelets. Lysis can be accomplished through chemical means (i.e. $CaCl_2$), osmotic means (use of distilled $H_2O$) or through freezing/thawing procedures. Platelet lysate can be derived from whole blood as described in U.S. Pat. No. 5,198,357. Platelet lysate is preferably prepared as described in PCT/GB12/052911 (published as WO 2013/076507). For instance, it may be prepared by subjecting a population of platelets to at least one freeze-thaw cycle, wherein the freeze portion of each cycle is carried out at a temperature lower than or equal to −78° C.

The adhesive and/or gel preferably comprises (a) platelet lysate, (b) at least one ioMPly acceptable polymer and (c) at least one ioMPly acceptable positively charged chemical species selected from the group consisting of lysine, arginine, histidine, aspartic acid, glutamic acid, alanine, methionine, proline, serine, asparagine, cysteine, polyamino acids, protamine, aminoguanidine, zinc ions and magnesium ions, wherein the composition is an aqueous gel having a viscosity in the range of 1000 to 500,000 mPa·s (cps) at room temperature. The ioMPly acceptable polymer is preferably cellulose or a poloaxmer. It may be any of the celluloses and poloaxmers discussed above.

The platelet lysate is preferably human platelet lysate. Platelet lysate is discussed in more detail above.

The hybrid composition may be contained within one or more liposomes or one or more microbubbles. Such structures are known in the art.

The following Examples illustrate the invention.

EXAMPLES

Example 1—Bone Marrow and Peripheral Blood Isolation & Expansion of ioMP Cells A bone marrow sample was diluted with Hank Buffered Saline Solution and layered over Ficoll-Paque for the isolation of mononuclear cells (MCs) by centrifugation. The MCs were then re-suspended in Hank Buffered Saline Solution and counted using 0.4% trypan blue exclusion assay to assess cellular viability. Cells were seeded in T25 flasks (in 5 ml of cell culture media, αMEM, GlutaMAX, penicillin-streptomycin, platelet lysate, heparin), and incubated at 37° C., 5% CO2. On day 8 the media was changed. Cells were monitored daily for observation of iMP-like cells (the subject of International Patent Application No. PCT/GB2015/051673; WO 2015/189587) and, if present, the iMP cells were epigenetically modified to form ioMP cells. This was done by seeding the iMP cells at 5000 per $cm^2$ in T25 flasks (in 5 ml of cell culture media, αMEM, GlutaMAX, penicillin-streptomycin, platelet lysate, heparin, L-Alanine, Sodium Phosphate Monobasic (anhydrous), 2'-Deoxyguanosine), and incubating them at 37° C., 5.3% CO2. O2 was reduced by 0.05%. Cells were monitored daily for observation of ioMP-like cells and, if present, harvested using cell dissociating solution according to manufacturer's instructions and sub-cultured in the same media as above. Cells were cryopreserved in passage 2 in culture media supplemented with 10% dimethyl sulfoxide to −80° C. and stored in liquid nitrogen for later use.

Example 2—HT-FACS Analysis

High-throughput fluorescence activated cell sorting (HT-FACS) analysis is a high-throughput screening platform which can rapidly characterize the cell surface phenotype of cells in suspension, with over 370 cell surface markers currently in the panel. This platform has undergone extensive validation and has been performed on many types of human tissues and cells. The panel consists of 370 human cell surface-specific antibodies arrayed in 96-well plates.

The aim was to determine the surface antigen expression profile of human ioMP cells of the invention, in comparison to human MSCs obtained from Lonza® and the applicant's proprietary immunomodulatory progenitor (IMP) cells. IMP cells are the subject of International Patent Application No. PCT/GB2015/051673 (WO 2015/189587). The high-throughput-FACS (HT-FACS) platform allows the screening of up to 370 surface antigens.

One vial of cryopreserved PB-MSCs (1×106 cells/ml) was seeded in a T75 cm2 flask containing 15 mL of CTL media (37° C., 5% CO2). Cells were grown until confluence of 80-90% changing the media every 2-3 days. To passage the cells, the media was removed and cells were washed twice with PBS. Cells were treated with 3 ml of Trypsin 0.25% until detached. Eight ml of media were added to inactivate the trypsin and cells were collected by centrifugation at 400 g for 5 min. Cells were re-suspended in 5 ml of media and seeded in a T175 cm2 flask containing 30 mL of CTL media (37° C., 5% CO2). Between 8 to 10 T175 cm2 flasks at 80-90% confluence were required to harvest 20-30 million cells (at passage 4) for the HT-FACS screening. In order to obtain a sufficient number of flow cytometry "events" per antibody, approximately 20 million viable cells is optimal. To collect the cells, the media was removed and cells were washed twice with PBS. Cells were treated with 5 ml of Trypsin 0.25% until detached. Media was added (8 ml) to inactivate the trypsin and collect the cells. Cells were centrifuged at 400 g for 5 min. The cell pellets were re-suspended (single-cell suspension) in 5 ml total of HBSS (Hank's Balanced Salt Solution minus calcium/magnesium, supplemented with 2 mM EDTA and 1% BSA). One aliquot of the sample (10 µl) was used to determine the total number of viable cells by using exclusion dye (0.2% trypan blue).

100 µl of sample were loaded into each well (about 40,000 cells per well assuring the collection of 10,000 to 20,000 events in the FACS). The samples were run in a BD FACSDiva upgraded with a BD High Throughput Sampler (automated sampler). The analysis of flow cytometry data were performed using FlowJo Software. The results were provided in plots, and an Excel spreadsheet containing the percentage of positive cells and median fluorescence intensity (MFI) for each antibody.

TABLE 1

Results of the HT-FACS analysis

| Marker | ioMP cells | | IMP cells | | BM-MSC (Lonza) | |
|---|---|---|---|---|---|---|
| | % cells | MFI | % cells | MFI | % cells | MFI |
| BLTR-1 | 2.01 | 308 | 6.7 | 207 | 1.37 | 214 |
| B2-microglobulin | 100 | 9119 | 99.8 | 5241 | 100 | 7522 |
| CA9 | 1.95 | 296 | 5.22 | 219 | 0 | ¥ |
| CDH3 | 1.93 | 326 | 2.93 | 198 | 0.475 | 257 |
| CDH6 | 0.0518 | 167 | 0.6 | 229 | 0.235 | 295 |
| CDH11 | 92.2 | 394 | 61.6 | 349 | 0.88 | 297 |
| CDw93 | 1.5 | 250 | 11.5 | 289 | 4.75 | 407 |
| CDw198 | 10.3 | 323 | 10.6 | 229 | 5.17 | 694 |
| CDw199 | 0.0628 | 841 | 17.2 | 262 | 2.54 | 469 |
| CDw210 | 30.1 | 344 | 10.8 | 239 | 0.622 | 246 |
| CDw218a | 2.97 | 361 | 0.384 | 192 | 0 | ¥ |
| CDw329 | 0.0604 | 368 | 0.182 | 305 | 0 | ¥ |
| CD1a | 0.113 | 442 | 0.338 | 258 | 0.28 | 198 |
| CD1b | 0.99 | 275 | 0.766 | 255 | 0.745 | 465 |
| CD1c | 3.02 | 307 | 15.7 | 246 | 0.926 | 165 |
| CD1d | 0.0547 | 424 | 2.7 | 219 | 0 | ¥ |
| CD2 | 0.703 | 339 | 0.292 | 242 | 0.526 | 553 |
| CD3 | 0.0396 | 435 | 0.158 | 249 | 0 | ¥ |
| CD3e | 0.0262 | 126 | 0.087 | 236 | 0 | ¥ |
| CD4 | 0.0364 | 226 | 1.11 | 235 | 0.157 | 398 |
| CD5 | 0.0303 | 378 | 0.151 | 215 | 0.34 | 1012 |
| CD6 | 0.989 | 409 | 1.04 | 253 | 2.68 | 521 |
| CD7 | 0.0659 | 225 | 0.239 | 182 | 0.24 | 187 |
| CD8 | 0.00926 | 457 | 0.214 | 242 | 0 | ¥ |
| CD8b | 0.092 | 304 | 4.34 | 311 | 0.705 | 660 |
| CD9 | 29.1 | 407 | 38.1 | 267 | 51.9 | 1061 |
| CD10 | 89 | 930 | 90.6 | 580 | 87.1 | 1105 |
| CD11a | 0.393 | 269 | 1.57 | 195 | 0 | ¥ |
| CD11b | 0.0128 | 467 | 6.24 | 218 | 0 | ¥ |
| CD11c | 0.269 | 382 | 1.8 | 203 | 0 | ¥ |
| CD13 | 100 | 61317 | 100 | 40326 | 100 | 35998 |
| CD14 | 0.121 | 356 | 8.03 | 244 | 6.25 | 325 |
| CD15 | 0.026 | 155 | 0.137 | 226 | 0.474 | 216 |
| CD16 | 2.41 | 296 | 10.1 | 209 | 3.73 | 219 |
| CD16b | 0.0348 | 446 | 0.331 | 261 | 0 | ¥ |
| CD17 | 7.32 | 295 | 20.9 | 424 | 0.462 | 297 |
| CD18 | 0.0771 | 406 | 0.65 | 184 | 0 | ¥ |
| CD19 | 0.0103 | 457 | 0.21 | 189 | 0 | ¥ |
| CD20 | 0.00751 | 180 | 0.176 | 253 | 0 | ¥ |
| CD21 | 0.985 | 309 | 0.66 | 235 | 0 | ¥ |
| CD22 | 0.271 | 262 | 0.596 | 185 | 0 | ¥ |
| CD23 | 0.137 | 391 | 0.551 | 232 | 0.234 | 257 |
| CD24 | 0.242 | 488 | 0.987 | 232 | 4 | 1662 |
| CD25 | 1.59 | 305 | 1.44 | 208 | 1.67 | 337 |
| CD26 | 50.9 | 519 | 21.3 | 295 | 6.33 | 661 |
| CD27 | 0.0347 | 430 | 0.409 | 231 | 0 | ¥ |
| CD28 | 0.222 | 299 | 0.643 | 212 | 0 | ¥ |
| CD29 | 100 | 2181 | 100 | 1382 | 100 | 6332 |
| CD30 | 0.529 | 278 | 0.446 | 239 | 0 | ¥ |
| CD31 | 0.596 | 433 | 1.29 | 251 | 0.214 | 231 |
| CD32 | 0.182 | 335 | 0.698 | 211 | 3.46 | 266 |
| CD33 | 0.259 | 449 | 1.25 | 189 | 0.372 | 364 |
| CD34 | 0.00731 | 496 | 0.287 | 227 | 0.885 | 181 |
| CD35 | 0.0136 | 630 | 0.134 | 225 | 0 | ¥ |
| CD36 | 0.292 | 497 | 0.458 | 258 | 3.57 | 340 |
| CD37 | 0.0341 | 376 | 0.0917 | 175 | 0.182 | 198 |
| CD38 | 0.0293 | 515 | 0.28 | 236 | 0 | ¥ |
| CD39 | 0.0625 | 234 | 0.126 | 237 | 21.8 | 1256 |
| CD40 | 0.0152 | 386 | 0.132 | 267 | 3.12 | 250 |
| CD41a | 0.172 | 446 | 0.293 | 240 | 0 | ¥ |
| CD41b | 0.0418 | 214 | 0.075 | 203 | 0 | ¥ |
| CD42a | 2.04 | 488 | 0.528 | 261 | 0.131 | 161 |
| CD42b | 0.237 | 272 | 7.29 | 234 | 0 | ¥ |
| CD43 | 0.047 | 436 | 0.406 | 218 | 1.81 | 166 |
| CD44 | 99.9 | 2234 | 99.9 | 8128 | 99.7 | 5215 |
| CD45 | 0.0368 | 441 | 0.271 | 235 | 0 | ¥ |
| CD45RA | 0.146 | 300 | 5.18 | 198 | 2.99 | 30865 |
| CD45RB | 0.0245 | 149 | 0.283 | 240 | 0.671 | 170 |
| CD45RO | 0.062 | 440 | 0.57 | 224 | 0 | ¥ |
| CD46 | 74.4 | 338 | 78.1 | 346 | 22.5 | 487 |
| CD47 | 100 | 1178 | 92.3 | 338 | 99.9 | 1885 |
| CD48 | 0.024 | 298 | 0.141 | 223 | 0.125 | 841 |
| CD49a | 84 | 610 | 24 | 254 | 51.5 | 883 |
| CD49b | 96.4 | 906 | 97.7 | 970 | 45.8 | 812 |

TABLE 1-continued

Results of the HT-FACS analysis

| Marker | ioMP cells % cells | MFI | IMP cells % cells | MFI | BM-MSC (Lonza) % cells | MFI |
|---|---|---|---|---|---|---|
| CD49c | 95.8 | 761 | 99.9 | 1998 | 99.6 | 5099 |
| CD49d | 92 | 664 | 93.7 | 493 | 26 | 477 |
| CD49e | 100 | 7191 | 100 | 5717 | 99.8 | 4427 |
| CD49f | 14.5 | 380 | 93.3 | 628 | 24.1 | 561 |
| CD50 | 0 | ¥ | 0.244 | 226 | 0.8 | 237 |
| CD51/CD61 | 94.1 | 603 | 92.7 | 384 | 68 | 792 |
| CD52 | 0.0948 | 275 | 0.218 | 203 | 0.128 | 155 |
| CD53 | 0.0457 | 330 | 1.66 | 210 | 0.292 | 507 |
| CD54 | 73.7 | 961 | 23.1 | 260 | 23.7 | 1034 |
| CD55 | 99.6 | 1894 | 94.5 | 583 | 52.5 | 790 |
| CD56 | 0.468 | 431 | 3.05 | 260 | 4.71 | 653 |
| CD57 | 0.0691 | 270 | 0.193 | 253 | 0 | ¥ |
| CD58 | 100 | 1195 | 99.7 | 932 | 98.1 | 1634 |
| CD59 | 100 | 3500 | 100 | 4757 | 100 | 13724 |
| CD60b | 31 | 337 | 34 | 508 | 10.9 | 580 |
| CD61 | 89.6 | 479 | 81.8 | 313 | 56.7 | 672 |
| CD62E | 0.324 | 465 | 2.33 | 263 | 1.03 | 695 |
| CD62L | 0.426 | 461 | 0.432 | 224 | 0.151 | 165 |
| CD62P | 0.156 | 402 | 0.325 | 242 | 0.924 | 1336 |
| CD63 | 86.9 | 710 | 99.1 | 1565 | 95.8 | 1736 |
| CD64 | 0.037 | 412 | 0.263 | 220 | 0.225 | 220 |
| CD65 | 0.578 | 295 | 0.825 | 236 | 0 | ¥ |
| CD65s | 1.93 | 272 | 7.62 | 265 | 0.539 | 379 |
| CD66 | 0.111 | 276 | 0.474 | 214 | 0.737 | 506 |
| CD66b | 0.0521 | 277 | 0.129 | 187 | 0 | ¥ |
| CD66c | 13.8 | 326 | 23.4 | 243 | 7.33 | 351 |
| CD66d | 0.812 | 358 | 2.06 | 212 | 0.322 | 216 |
| CD66e | 69.4 | 411 | 56.1 | 269 | 13.6 | 537 |
| CD69 | 0.0189 | 5228 | 0.296 | 236 | 0.279 | 324 |
| CD70 | 0.069 | 259 | 0.36 | 211 | 0.187 | 190 |
| CD71 | 45.6 | 420 | 51 | 267 | 4.71 | 334 |
| CD72 | 0.041 | 164 | 0.036 | 191 | 0.334 | 334 |
| CD73 | 99.9 | 5746 | 100 | 6332 | 99.8 | 5591 |
| CD74 | 0.192 | 281 | 0.177 | 202 | 0.587 | 875 |
| CD75 | 0.0331 | 389 | 0.0789 | 195 | 0.304 | 248 |
| CD77 | 0.0691 | 224 | 7.15 | 375 | 2.4 | 343 |
| CD79a | 0.228 | 331 | 15.4 | 224 | 0.45 | 240 |
| CD79b | 1.4 | 293 | 4.87 | 204 | 0.317 | 177 |
| CD80 | 5.98 | 432 | 2.94 | 208 | 4.57 | 536 |
| CD81 | 100 | 5254 | 100 | 3950 | 99.9 | 5920 |
| CD82 | 99.9 | 2910 | 96.3 | 849 | 82.7 | 1268 |
| CD83 | 0.53 | 289 | 27.9 | 246 | 1.34 | 291 |
| CD84 | 3.45 | 310 | 7.94 | 197 | 4.1 | 394 |
| CD85a | 1.29 | 305 | 6.76 | 210 | 0.971 | 898 |
| CD85d | 43.3 | 363 | 17 | 240 | 0.98 | 201 |
| CD85g | 34.5 | 354 | 47.2 | 300 | 6.15 | 211 |
| CD85h | 9.43 | 340 | 15.6 | 216 | 0 | ¥ |
| CD85j | 44.6 | 368 | 20.6 | 253 | 0.221 | 262 |
| CD86 | 4.2 | 318 | 24.7 | 258 | 0.702 | 232 |
| CD87 | 1.69 | 426 | 0.178 | 239 | 1.61 | 277 |
| CD88 | 0.098 | 320 | 1.32 | 225 | 0.352 | 397 |
| CD89 | 4.88 | 322 | 5.73 | 208 | 0.244 | 738 |
| CD90 | 95.7 | 206000 | 100 | 67835 | 99.3 | 1.25E+05 |
| CD91 | 97.9 | 857 | 95.5 | 543 | 63.4 | 783 |
| CD92 | 98.6 | 547 | 35.4 | 255 | 33.3 | 717 |
| CD94 | 0.03 | 154 | 0.121 | 199 | 0.321 | 193 |
| CD95 | 100 | 2684 | 98.9 | 566 | 66.7 | 1532 |
| CD96 | 21.2 | 332 | 21 | 250 | 2.63 | 221 |
| CD97 | 0.191 | 259 | 1.64 | 220 | 0.434 | 242 |
| CD98 | 99.9 | 7355 | 100 | 2697 | 99.9 | 6944 |
| CD99 | 5.01 | 327 | 24.8 | 246 | 0.224 | 296 |
| CD100 | 0.0719 | 361 | 0.103 | 250 | 0.132 | 898 |
| CD101 | 0.334 | 280 | 0.29 | 216 | 0 | ¥ |
| CD102 | 0.142 | 382 | 9.24 | 249 | 2.91 | 381 |
| CD103 | 0.0312 | 127 | 0.152 | 225 | 0.297 | 381 |
| CD104 | 0.806 | 338 | 4.06 | 227 | 99.3 | 3019 |
| CD105 | 99.8 | 1223 | 99.9 | 1988 | 100 | 2710 |
| CD106 | 18.7 | 351 | 6.93 | 266 | 4.64 | 457 |
| CD107a | 4.59 | 361 | 0.717 | 242 | 0.337 | 254 |
| CD107b | 1.13 | 263 | 0.221 | 261 | 0.225 | 205 |
| CD108 | 99.2 | 4110 | 99.7 | 10055 | 78 | 1774 |
| CD109 | 0.0726 | 375 | 1.89 | 205 | 0.253 | 237 |
| CD110 | 67.1 | 411 | 55.6 | 312 | 16.6 | 669 |
| CD111 | 88.4 | 589 | 90.7 | 374 | 0 | ¥ |

TABLE 1-continued

Results of the HT-FACS analysis

| Marker | ioMP cells | | IMP cells | | BM-MSC (Lonza) | |
|---|---|---|---|---|---|---|
| | % cells | MFI | % cells | MFI | % cells | MFI |
| CD112 | 12.1 | 334 | 12.1 | 237 | 0.64 | 258 |
| CD114 | 13 | 348 | 54.9 | 301 | 4.83 | 411 |
| CD115 | 99.9 | 1569 | 8.41 | 217 | 0 | ¥ |
| CD116 | 33.4 | 361 | 17 | 255 | 2.61 | 2213 |
| CD117 | 0.147 | 1115 | 31.5 | 284 | 2.56 | 1010 |
| CD118 | 13.8 | 328 | 67.4 | 317 | 0 | ¥ |
| CD119 | 98 | 645 | 78.5 | 295 | 24.8 | 497 |
| CD120a | 87.8 | 438 | 38.1 | 240 | 0 | ¥ |
| CD120b | 4.77 | 325 | 1.11 | 195 | 0.297 | 162 |
| CD121b | 54.6 | 770 | 39.8 | 311 | 2.75 | 381 |
| CD122 | 43.6 | 365 | 41.7 | 283 | 4.56 | 343 |
| CD123 | 13.5 | 339 | 46.9 | 314 | 7.06 | 495 |
| CD124 | 5.5 | 306 | 1.52 | 194 | 0.225 | 603 |
| CD125 | 4.24 | 338 | 19.5 | 319 | 0 | ¥ |
| CD126 | 5.62 | 325 | 7.05 | 214 | 0.709 | 742 |
| CD127 | 0.0103 | 481 | 18.5 | 548 | 12.5 | 611 |
| CD129 | 0.0603 | 428 | 0.178 | 197 | 0 | ¥ |
| CD130 | 85.7 | 449 | 83.6 | 326 | 8.15 | 311 |
| CD131 | 0.179 | 263 | 0.684 | 197 | 0 | ¥ |
| CD132 | 33.3 | 369 | 78.8 | 382 | 3.43 | 456 |
| CD133 | 0.0395 | 249 | 0.054 | 234 | 0 | ¥ |
| CD134 | 7.44 | 324 | 8.15 | 235 | 1.29 | 312 |
| CD135 | 2.42 | 309 | 5.18 | 206 | 0.575 | 686 |
| CD136 | 0.894 | 343 | 0.302 | 173 | 0 | ¥ |
| CD137 | 0.0279 | 433 | 0.392 | 194 | 0 | ¥ |
| CD137L | 75.7 | 441 | 13.5 | 278 | 15.6 | 539 |
| CD138 | 0.0299 | 138 | 0.227 | 207 | 0 | ¥ |
| CD140a | 2.25 | 291 | 4.1 | 184 | 0.98 | 249 |
| CD140b | 100 | 4987 | 89.1 | 695 | 97.8 | 1922 |
| CD141 | 2.74 | 393 | 21 | 334 | 0.385 | 398 |
| CD142 | 0.26 | 488 | 0.478 | 196 | 0.555 | 148 |
| CD143 | 2.3 | 327 | 29.3 | 279 | 0 | ¥ |
| CD144 | 0.0213 | 104 | 0.0728 | 193 | 0.159 | 112 |
| CD146 | 82.6 | 875 | 94.2 | 1744 | 89.5 | 1853 |
| CD147 | 100 | 5563 | 100 | 4780 | 100 | 3704 |
| CD148 | 94.8 | 487 | 84.6 | 311 | 0 | ¥ |
| CD150 | 3.18 | 338 | 0.467 | 217 | 0.364 | 204 |
| CD151 | 100 | 14835 | 100 | 10207 | 99.9 | 9421 |
| CD152 | 5.46 | 326 | 6.45 | 224 | 5.87 | 289 |
| CD153 | 10.5 | 343 | 10.9 | 226 | 1.19 | 359 |
| CD154 | 0.137 | 493 | 0.357 | 206 | 0.893 | 158 |
| CD155 | 100 | 5333 | 99.8 | 2312 | 100 | 2975 |
| CD156b | 46.3 | 368 | 81 | 318 | 36.4 | 475 |
| CD157 | 15.7 | 419 | 0.713 | 236 | 6.33 | 419 |
| CD158a | 0.0398 | 157 | 0.0919 | 248 | 0.22 | 330 |
| CD158b | 0.0115 | 394 | 0.129 | 170 | 0.195 | 134 |
| CD158b2 | 3.38 | 324 | 2.54 | 196 | 0 | ¥ |
| CD158d | 4.55 | 314 | 56.3 | 249 | 1.56 | 311 |
| CD158e2 | 0.0395 | 411 | 0.254 | 194 | 0 | ¥ |
| CD158f | 11.9 | 349 | 25 | 257 | 0 | ¥ |
| CD158i | 2.88 | 309 | 21.9 | 289 | 3.12 | 277 |
| CD159a | 2.8 | 300 | 6.57 | 209 | 0.462 | 1485 |
| CD159c | 0.975 | 272 | 2.44 | 194 | 0.917 | 15099 |
| CD160 | 0.0427 | 224 | 1.07 | 236 | 0.9 | 436 |
| CD161 | 19.2 | 340 | 5.95 | 212 | 3.64 | 217 |
| CD162 | 2.56 | 440 | 13.2 | 246 | 4.41 | 222 |
| CD163 | 0.0478 | 129 | 0.197 | 205 | 0 | ¥ |
| CD164 | 60.2 | 455 | 11.9 | 232 | 27 | 365 |
| CD165 | 8.21 | 313 | 0.716 | 203 | 3.55 | 333 |
| CD166 | 100 | 2375 | 99.9 | 1658 | 99.8 | 5522 |
| CD167 | 6.58 | 318 | 0.496 | 224 | 7.69 | 186 |
| CD169 | 18.1 | 340 | 1.76 | 202 | 0.178 | 236 |
| CD170 | 1.43 | 368 | 11.9 | 221 | 74.3 | 1112 |
| CD171 | 0.259 | 276 | 1.9 | 190 | 0 | ¥ |
| CD172a | 56.4 | 363 | 61.8 | 265 | 3.33 | 336 |
| CD172b | 0.0416 | 492 | 0.0955 | 227 | 0.285 | 225 |
| CD172g | 5.61 | 307 | 14.5 | 239 | 7.14 | 276 |
| CD175s | 93 | 406 | 96.2 | 526 | 27.1 | 542 |
| CD177 | 4.82 | 285 | 0.477 | 225 | 0.46 | 458 |
| CD178 | 76.3 | 449 | 51.6 | 295 | 0.49 | 174 |
| CD179a | 23.4 | 348 | 6.31 | 210 | 1.84 | 374 |
| CD180 | 6.24 | 330 | 0.824 | 203 | 0.478 | 759 |
| CD181 | 38.5 | 366 | 85 | 400 | 2.55 | 320 |
| CD182 | 1.06 | 379 | 68.8 | 315 | 4.31 | 375 |

TABLE 1-continued

Results of the HT-FACS analysis

| Marker | ioMP cells % cells | ioMP cells MFI | IMP cells % cells | IMP cells MFI | BM-MSC (Lonza) % cells | BM-MSC (Lonza) MFI |
|---|---|---|---|---|---|---|
| CD183 | 3.3 | 329 | 3.08 | 198 | 0 | ¥ |
| CD184 | 0.0618 | 257 | 0.219 | 264 | 0.775 | 204 |
| CD185 | 2.45 | 280 | 6.04 | 258 | 1.39 | 285 |
| CD186 | 65.1 | 537 | 1.48 | 229 | 41.5 | 839 |
| CD191 | 0.456 | 295 | 12.6 | 224 | 0 | ¥ |
| CD192 | 0.051 | 305 | 0.0662 | 235 | 0.0497 | 335 |
| CD193 | 62.3 | 413 | 51 | 309 | 8.16 | 393 |
| CD194 | 0.0951 | 237 | 7.13 | 261 | 0 | ¥ |
| CD195 | 0.164 | 323 | 1.02 | 248 | 1.94 | 8169 |
| CD196 | 58.8 | 387 | 46.3 | 259 | 2.8 | 333 |
| CD197 | 0.0126 | 568 | 0.159 | 165 | 0 | ¥ |
| CD200 | 11.5 | 433 | 0.594 | 214 | 0.912 | 170 |
| CD201 | 64.8 | 424 | 55.7 | 277 | 0.858 | 269 |
| CD202b | 75.7 | 425 | 82.7 | 353 | 23.2 | 708 |
| CD203c | 47.6 | 371 | 8.66 | 241 | 0 | ¥ |
| CD204 | 8 | 316 | 13.7 | 249 | 1.44 | 379 |
| CD205 | 0.928 | 322 | 4.94 | 219 | 0 | ¥ |
| CD206 | 0.0296 | 101 | 0.205 | 231 | 0 | ¥ |
| CD207 | 0.0479 | 130 | 0.0679 | 231 | 2.7 | 429 |
| CD208 | 1.78 | 305 | 3.27 | 200 | 0 | ¥ |
| CD209 | 0.0161 | 429 | 0.153 | 259 | 0 | ¥ |
| CD212 | 0.0453 | 432 | 0.476 | 181 | 0.127 | 229 |
| CD213a2 | 19.6 | 406 | 8.7 | 280 | 8 | 818 |
| CD215 | 16.5 | 339 | 14.6 | 238 | 0.86 | 291 |
| CD217 | 4.12 | 337 | 29.8 | 259 | 35.8 | 567 |
| CD218b | 13.3 | 326 | 23.4 | 259 | 0.463 | 349 |
| CD220 | 0.171 | 320 | 2.93 | 246 | 1.5 | 678 |
| CD221 | 76.3 | 384 | 3.16 | 195 | 1.1 | 515 |
| CD222 | 22.2 | 317 | 8.09 | 278 | 0.768 | 226 |
| CD223 | 32.8 | 350 | 38.9 | 289 | 0 | ¥ |
| CD226 | 0.154 | 455 | 1.15 | 172 | 0.22 | 126 |
| CD227 | 53.2 | 370 | 4.87 | 298 | 5.79 | 474 |
| CD229 | 0.106 | 417 | 0.579 | 216 | 5.56 | 123 |
| CD230 | 100 | 6756 | 99.9 | 2381 | 100 | 1470 |
| CD231 | 76.6 | 458 | 34.2 | 282 | 34.8 | 675 |
| CD234 | 20.2 | 356 | 7.7 | 217 | 0.397 | 229 |
| CD235a | 52.2 | 381 | 55.8 | 275 | 5.11 | 400 |
| CD243 (BC) | 6.94 | 361 | 20.8 | 250 | 2.31 | 303 |
| CD243 (BD) | 0.0112 | 141 | 0.208 | 203 | 0 | ¥ |
| CD244 | 0.336 | 363 | 0.548 | 195 | 0 | ¥ |
| CD245 | 62.1 | 381 | 99.2 | 1286 | 13.3 | 226 |
| CD249 | 0.77 | 286 | 19.7 | 254 | 0 | ¥ |
| CD252 | 82.2 | 551 | 21.4 | 697 | 20.6 | 1044 |
| CD253 | 0.183 | 406 | 44.1 | 357 | 7.07 | 777 |
| CD254 | 16.6 | 323 | 12.3 | 229 | 3.85 | 393 |
| CD255 | 8.96 | 331 | 10.1 | 233 | 0.437 | 175 |
| CD256 | 82.6 | 464 | 7.94 | 204 | 0.792 | 289 |
| CD257 | 90.3 | 623 | 63.2 | 271 | 5.03 | 408 |
| CD258 | 0.944 | 309 | 3.17 | 182 | 0 | ¥ |
| CD261 | 13.5 | 330 | 30.3 | 275 | 21.4 | 1259 |
| CD262 | 11.8 | 370 | 12.1 | 222 | 4.55 | 1097 |
| CD263 | 3.81 | 344 | 1.47 | 248 | 0 | ¥ |
| CD264 | 55.2 | 411 | 44.9 | 284 | 9.09 | 141 |
| CD267 | 75.9 | 645 | 91.8 | 640 | 36.6 | 708 |
| CD268 | 7.78 | 495 | 64.6 | 379 | 13.5 | 742 |
| CD269 | 5.57 | 326 | 8.51 | 214 | 2.4 | 223 |
| CD270 | 47.2 | 370 | 31.6 | 258 | 8.79 | 499 |
| CD271 | 1.28 | 415 | 1.63 | 275 | 10.4 | 812 |
| CD272 | 68.4 | 418 | 33.2 | 536 | 12.3 | 959 |
| CD273 | 43.8 | 430 | 92.4 | 395 | 51.7 | 763 |
| CD274 | 1.36 | 296 | 23.9 | 220 | 1.12 | 276 |
| CD275 | 1.16 | 309 | 26 | 257 | 0.904 | 279 |
| CD276 | 100 | 11060 | 100 | 4110 | 97.8 | 1749 |
| CD277 | 0.312 | 300 | 1.55 | 189 | 0 | ¥ |
| CD278 | 0.0202 | 120 | 0.147 | 158 | 0.0836 | 262 |
| CD279 | 11.4 | 330 | 5.5 | 212 | 0.492 | 203 |
| CD281 | 0.0598 | 453 | 54.7 | 290 | 2.12 | 309 |
| CD282 | 0.0769 | 167 | 0.101 | 207 | 0.529 | 427 |
| CD283 | 66.5 | 402 | 68.9 | 337 | 6.92 | 826 |
| CD284 | 3.02 | 315 | 7.94 | 216 | 0.84 | 1.36E+05 |
| CD286 | 68.5 | 413 | 76.9 | 357 | 11.4 | 489 |
| CD288 | 88.4 | 648 | 85.6 | 563 | 11.2 | 412 |
| CD289 | 5.15 | 323 | 11.3 | 249 | 0.359 | 251 |
| CD290 | 64.2 | 390 | 45.1 | 296 | 9.5 | 450 |

TABLE 1-continued

Results of the HT-FACS analysis

| Marker | ioMP cells % cells | ioMP cells MFI | IMP cells % cells | IMP cells MFI | BM-MSC (Lonza) % cells | BM-MSC (Lonza) MFI |
|---|---|---|---|---|---|---|
| CD292 | 2.83 | 281 | 2.39 | 223 | 0.522 | 244 |
| CD294 | 0.00935 | 212 | 8.81 | 246 | 34.1 | 646 |
| CD295 | 95.2 | 571 | 49 | 234 | 73.7 | 941 |
| CD298 | 7.86 | 2826 | 99.8 | 2052 | 98.9 | 1844 |
| CD299 | 47.8 | 367 | 29.5 | 262 | 1.07 | 311 |
| CD300a | 5.45 | 321 | 1.82 | 188 | 0.222 | 184 |
| CD300c | 31.6 | 346 | 37.3 | 272 | 3.76 | 403 |
| CD300e | 69.3 | 416 | 38.7 | 296 | 0.697 | 246 |
| CD301 | 0.777 | 326 | 3.39 | 260 | 0.626 | 1167 |
| CD303 | 0.0228 | 477 | 66.8 | 369 | 3.33 | 353 |
| CD304 | 9.14 | 318 | 65.2 | 281 | 0.502 | 194 |
| CD305 | 3.7 | 314 | 4.12 | 208 | 0.972 | 794 |
| CD307 | 14 | 322 | 7.08 | 229 | 0.305 | 209 |
| CD309 | 65.3 | 398 | 34.4 | 246 | 14.2 | 538 |
| CD312 | 56 | 388 | 24.8 | 255 | 12.2 | 515 |
| CD314 | 20.5 | 338 | 38.5 | 264 | 11.6 | 12632 |
| CD317 | 13 | 371 | 48.9 | 320 | 25 | 742 |
| CD318 | 39.7 | 414 | 71.7 | 451 | 12.3 | 499 |
| CD319 | 21.1 | 340 | 27.8 | 261 | 21.9 | 708 |
| CD321 | 16.7 | 415 | 3.81 | 232 | 5.04 | 532 |
| CD322 | 0.00557 | 375 | 4.37 | 298 | 0.248 | 376 |
| CD324 | 7.15 | 327 | 17.2 | 268 | 0.387 | 1206 |
| CD325 | 5.66 | 328 | 3.83 | 212 | 0.501 | 274 |
| CD326 | 25.1 | 394 | 18.1 | 230 | 0.463 | 378 |
| CD328 | 43.5 | 369 | 32 | 251 | 1.99 | 302 |
| CD332 | 0.0229 | 32055 | 0.814 | 253 | 0.181 | 2600 |
| CD333 | 18.2 | 334 | 7.78 | 242 | 1.01 | 234 |
| CD334 | 0.178 | 393 | 1.35 | 187 | 1.76 | 347 |
| CD335 | 0.303 | 282 | 0.669 | 201 | 0.274 | 149 |
| CD336 | 0.137 | 469 | 0.544 | 203 | 0.212 | 180 |
| CD337 | 75.5 | 460 | 87.3 | 572 | 26.4 | 738 |
| CD338 | 72.6 | 425 | 49 | 263 | 19.5 | 639 |
| CD339 | 1.88 | 260 | 1.76 | 227 | 1.22 | 369 |
| CD340 | 99.9 | 991 | 94.9 | 401 | 41 | 541 |
| CD344 | 92 | 556 | 65.5 | 305 | 17.5 | 600 |
| CD349 | 91.3 | 756 | 87.6 | 471 | 80.3 | 1408 |
| CD351 | 0.512 | 376 | 76.4 | 415 | 28.1 | 681 |
| CD352 | 65.8 | 454 | 0.518 | 208 | 0.394 | 528 |
| CD354 | 28.1 | 350 | 13.6 | 244 | 1.66 | 350 |
| CD355 | 0.277 | 351 | 10.4 | 245 | 1.24 | 239 |
| CD357 | 62.8 | 406 | 10.4 | 249 | 1.95 | 498 |
| CD358 | 33.6 | 358 | 45.1 | 297 | 7.63 | 517 |
| CD360 (BD) | 93.1 | 722 | 24.9 | 259 | 3.53 | 371 |
| CD360 (BL) | 0.0438 | 328 | 33 | 293 | 4.5 | 380 |
| CD362 | 38.5 | 353 | 14.7 | 274 | 0.774 | 353 |
| CD363 | 1.28 | 350 | 18.7 | 242 | 0.757 | 337 |
| CLA | 0.0833 | 369 | 0.277 | 2363 | 9.23 | 358 |
| CLIP | 0.029 | 331 | 0.138 | 194 | 0 | ¥ |
| DCIR | 3.34 | 275 | 0.264 | 234 | 0.15 | 250 |
| EGF-R | 0.0459 | 337 | 33.3 | 231 | 2.02 | 263 |
| FMC7 | 100 | 4722 | 0.0776 | 249 | 0 | ¥ |
| HLA-ABC | 0.0844 | 224 | 99.9 | 1936 | 99.8 | 2932 |
| HLA-A2 | 0.967 | 371 | 3.52 | 198 | 20.9 | 5717 |
| HLA-DM | 0.599 | 327 | 0.172 | 174 | 0.14 | 181 |
| HLA-DR | 6.94 | 370 | 0.247 | 226 | 0.481 | 1662 |
| HPC | 0.103 | 427 | 2.14 | 223 | 6.31 | 359 |
| ITGB7 | 99.9 | 2289 | 0.34 | 262 | 0.159 | 208 |
| LTBR | 0.325 | 313 | 34.5 | 524 | 87.6 | 1178 |
| Lgr-5 | 1.5 | 318 | 9.8 | 233 | 0.328 | 138 |
| MIC A/B | 0.0236 | 242 | 97.1 | 441 | 4.01 | 513 |
| Notch1 | 90.2 | 655 | 20.5 | 266 | 22.8 | 534 |
| Notch2 | 0.121 | 309 | 95.8 | 588 | 2.15 | 450 |
| Notch3 | 7.93 | 307 | 5.37 | 243 | 0.971 | 398 |
| PAC-1 | 0.0145 | 511 | 0.137 | 287 | 2.91 | 1142 |
| Podoplanin | 60.2 | 395 | 8.81 | 265 | 0.395 | 221 |
| SSEA-3 | 20.1 | 532 | 20.7 | 370 | 2.44 | 460 |
| SSEA-4 | 79.6 | 723 | 87.4 | 730 | 6.27 | 519 |
| Stro-1 | 0.0453 | 331 | 18.5 | 268 | 0.195 | 421 |
| TCR alpha beta | 1.18 | 429 | 0.327 | 208 | 11.1 | 649 |
| TCR gamma delta | 56.4 | 430 | 52.9 | 313 | 0.178 | 4504 |
| TPBG | 0.0191 | 410 | 0.197 | 246 | 3.93 | 348 |

TABLE 1-continued

Results of the HT-FACS analysis

| Marker | ioMP cells | | IMP cells | | BM-MSC (Lonza) | |
|---|---|---|---|---|---|---|
| | % cells | MFI | % cells | MFI | % cells | MFI |
| VB8 TCR | 37 | 355 | 25.1 | 281 | 12.1 | 434 |
| VD2 TCR | 23.9 | 80142 | 13.2 | 13689 | 0.641 | 246 |
| fMLP-R | 19 | 354 | 11.4 | 237 | n/a | n/a |

The invention claimed is:

1. A method of producing a population of immuno-oncology mesodermal progenitor (ioMP) cells, comprising (a) culturing mononuclear cells (MCs) in the presence of platelet lysate and low oxygen to induce the MCs to adhere and differentiate into immuno-modulatory progenitor (iMP) cells, (b) culturing the iMP cells in the presence of platelet lysate and low oxygen and in culture medium supplemented with one or more of L-Alanine, Sodium Phosphate Monobasic (anhydrous) and 2'-Deoxyguanosine to induce the iMP cells to adhere and differentiate into ioMP cells and (c) harvesting and culturing those ioMP cells, wherein
  (i) at least 60% of the cells in the population of ioMP cells express detectable levels of CD66e,
  (ii) at least 45% of the cells in the population of ioMP cells express detectable levels of CD121b,
  (iii) at least 35% of the cells in the population of ioMP cells express detectable levels of CD122,
  (iv) at least 50% of the cells in the population of ioMP cells express detectable levels of CD164,
  (v) at least 45% of the cells in the population of ioMP cells express detectable levels of CD172a,
  (vi) at least 35 of the cells in the population of ioMP cells express detectable levels of CD203c,
  (vii) at least 45% of the cells in the population of ioMP cells express detectable levels of CD264,
  (viii) at least 35% of the cells in the population of ioMP cells express detectable levels of CD270,
  (ix) at least 35% of the cells in the population of ioMP cells express detectable levels of CD328,
  (x) at least 50% of the cells in the population of ioMP cells express detectable levels of CD358 and
  (xi) at least 45% of the cells in the population of ioMP cells express detectable levels of TCR gamma delta;
  (xi) at least 95% of the cells in the population of ioMP cells express detectable levels of FMC, and
  (xii) at least 95% of the cells in the population of ioMP cells express detectable level of ITGB7;
  and wherein
  (a) 0.5% or fewer of the cells in the population of ioMP cells express detectable levels of HLA-ABC,
  (b) 0.5% or fewer of the cells in the population of ioMP cells express detectable levels of MIC A/B,
  (c) 0.5% or fewer of the cells in the population of ioMP cells express detectable levels of Notch2,
  (d) 0.5% or fewer of the cells in the population of ioMP cells express detectable levels of CD360,
  (e) 0.5% or fewer of the cells in the population of ioMP cells express detectable levels of CLIP, and
  (f) 0.1% or fewer of the cells in the population of ioMP cells express detectable levels of CD11b.

2. A method according to claim 1, wherein the MCs are peripheral blood mononuclear cells (PBMCs) or are primary MCs derived from bone marrow.

3. A method according to claim 1 or 2, wherein the MCs are obtained from a patient in to which the population of ioMPs will be administered or an allogeneic donor.

* * * * *